(12) United States Patent
Xu et al.

(10) Patent No.: US 12,390,154 B2
(45) Date of Patent: Aug. 19, 2025

(54) METHOD, APPARATUS AND SYSTEM OF MEASURING TISSUE ELEMENT, ELECTRONIC DEVICE AND STORAGE MEDIUM

(71) Applicant: SUNRISE TECHNOLOGIES CO., LTD., Beijing (CN)

(72) Inventors: Kexin Xu, Beijing (CN); Mingfei Yao, Beijing (CN)

(73) Assignee: SUNRISE TECHNOLOGIES CO., LTD, Beijing (CN)

( * ) Notice: Subject to any disclaimer, the term of this patent is extended or adjusted under 35 U.S.C. 154(b) by 228 days.

(21) Appl. No.: 18/005,211

(22) PCT Filed: May 12, 2021

(86) PCT No.: PCT/CN2021/093247
§ 371 (c)(1),
(2) Date: Jan. 12, 2023

(87) PCT Pub. No.: WO2022/012135
PCT Pub. Date: Jan. 20, 2022

(65) Prior Publication Data
US 2023/0263460 A1 Aug. 24, 2023

(30) Foreign Application Priority Data
Jul. 14, 2020 (CN) .......................... 202010673342.5

(51) Int. Cl.
*A61B 5/00* (2006.01)
(52) U.S. Cl.
CPC ............ *A61B 5/441* (2013.01); *A61B 5/0075* (2013.01); *A61B 5/6831* (2013.01)
(58) Field of Classification Search
CPC ...... A61B 5/441; A61B 5/0075; A61B 5/6831
See application file for complete search history.

(56) References Cited

U.S. PATENT DOCUMENTS 6,101,405 A 8/2000 Yasuda et al.
6,147,749 A 11/2000 Kubo et al.
(Continued)

FOREIGN PATENT DOCUMENTS

CN 1165556 A 11/1997
CN 1416780 A 5/2003
(Continued)

OTHER PUBLICATIONS

Notice of Reasons for Refusal, for Japanese Patent Application No. 2023-502869, dated Dec. 5, 2023, 10 pages.
(Continued)

*Primary Examiner* — Gerald Johnson
(74) *Attorney, Agent, or Firm* — Westman, Champlin & Koehler, P.A.

(57) ABSTRACT

Provided are a method, an apparatus and a system of measuring tissue element, an electronic device, and a medium. The method includes: acquiring a target image information of a target position of a tissue to be measured and a pre-stored template image information of a locating position, the target image information includes a surface target image and/or an internal target image, and the template image information includes a surface template image and/or an internal template image; determining the target position as the locating position in response to the target image information being matched with the template image information; determining a measurement position according to the locating position and a corresponding relationship between the locating position and the measurement position of the tissue to be measured, the measurement position is a position meeting a reproducibility; and performing a tissue element measurement at the measurement position.

17 Claims, 13 Drawing Sheets

(56) References Cited

U.S. PATENT DOCUMENTS

| | | | |
|---|---|---|---|
| 6,564,088 | B1 | 5/2003 | Soller et al. |
| 7,613,502 | B2 | 11/2009 | Yamamoto et al. |
| 8,135,447 | B2 | 3/2012 | Kondoh et al. |
| 8,194,942 | B2 | 6/2012 | Tobe et al. |
| 9,033,510 | B2 | 5/2015 | Narasimha-Lyer et al. |
| 10,092,178 | B2 | 10/2018 | Narasimha-Lyer et al. |
| 2001/0021803 | A1 | 9/2001 | Blank et al. |
| 2002/0019707 | A1 | 2/2002 | Cohen et al. |
| 2005/0075549 | A1 | 4/2005 | Kondoh et al. |
| 2006/0100526 | A1 | 5/2006 | Yamamoto et al. |
| 2010/0063369 | A1 | 3/2010 | Kondoh et al. |
| 2010/0278397 | A1 | 11/2010 | Tobe et al. |
| 2012/0249956 | A1 | 10/2012 | Narasimha-Lyer et al. |
| 2013/0121544 | A1 | 5/2013 | Sarrafzadeh et al. |
| 2015/0216454 | A1 | 8/2015 | Kasahara et al. |
| 2015/0327761 | A1 | 11/2015 | Narasimha-Lyer et al. |
| 2017/0000370 | A1 | 1/2017 | Hyde et al. |
| 2021/0038184 | A1* | 2/2021 | Shiromaru ............ A61B 8/54 |
| 2022/0054051 | A1 | 2/2022 | Xu et al. |

FOREIGN PATENT DOCUMENTS

| | | |
|---|---|---|
| CN | 1602797 A | 4/2005 |
| CN | 102939045 A | 2/2013 |
| CN | 103429142 A | 12/2013 |
| CN | 103892805 A | 7/2014 |
| CN | 107242855 A | 10/2017 |
| CN | 111317443 A | 6/2020 |
| JP | S53157592 U | 12/1978 |
| JP | H01118484 U | 8/1989 |
| JP | H11047119 A | 2/1999 |
| JP | 2004501380 A | 1/2004 |
| JP | 2004298547 A | 10/2004 |
| JP | 2004321574 A | 11/2004 |
| JP | 2006000180 A | 1/2006 |
| JP | 2006122086 A | 5/2006 |
| JP | 2009059249 A | 3/2009 |
| JP | 2015-112418 A | 6/2015 |
| JP | 2015142666 A | 8/2015 |
| WO | 2005107578 A1 | 11/2005 |

OTHER PUBLICATIONS

International Search Report and Written Opinion from International Application No. PCT/CN2021/093247, dated Aug. 2, 2021.
Office Action, including search report, for Chinese Patent Application No. 202010673342.5, dated Jun. 21, 2023, 21 pages.
Notice of Reasons for Refusal for Japanese patent application No. 2023-502869; date of drafting Jun. 21, 2024, 4 pages.
English translation of Notice of Reasons for Refusal for Japanese patent application No. 2023-502869; date of drafting Jun. 21, 2024, 4 pages.
Translation of Korean Office Action for corresponding Korean Application No. 10-2023-7004898, dated May 13, 2025, 16 pages.

* cited by examiner

METHOD, APPARATUS AND SYSTEM OF MEASURING TISSUE ELEMENT, ELECTRONIC DEVICE AND STORAGE MEDIUM

CROSS REFERENCE TO RELATED APPLICATION(S)

This application is a Section 371 National Stage Application of International Application No. PCT/CN2021/093247, filed on May 12, 2021, entitled "METHOD, APPARATUS AND SYSTEM OF MEASURING TISSUE ELEMENT, ELECTRONIC DEVICE AND STORAGE MEDIUM", which claims priority to Chinese Patent Application No. 202010673342.5, filed on Jul. 14, 2020, the disclosures of which are incorporated herein by reference in their entireties.

TECHNICAL FIELD

The present disclosure relates to a field of spectral measurement technology, and in particular to a method, an apparatus and a system of measuring tissue element, an electronic device and a storage medium.

BACKGROUND

A near-infrared historical spectral measurement method has characteristics of rapidness, non-invasiveness, and multidimensional information, etc., and is generally adopted to measure tissue element. The tissue element refers to an element in human blood, including blood sugar, hemoglobin, and fat, etc.

However, a tissue element to be measured has a weak absorption, and a variation range of a concentration of the tissue element to be measured in an object to be detected is not large, therefore, a valid signal to be measured is weak. Moreover, it is very vulnerable to an interference of a physiological noise, a measurement condition and an instrument noise, etc., which may even mask an information of the tissue element to be measured, thus making it difficult to extract the weak signal under an interference of a large background noise. The measurement condition includes a measurement position, a measurement temperature, a contact pressure, and so on.

SUMMARY

According to an aspect of the present disclosure, a method of measuring tissue element is provided, including: acquiring a target image information of a target position of a tissue to be measured and a pre-stored template image information of a locating position, the target image information includes a surface target image and/or an internal target image, and the template image information includes a surface template image and/or an internal template image; determining the target position as the locating position in response to the target image information being matched with the template image information; determining a measurement position according to the locating position and a corresponding relationship between the locating position and the measurement position of the tissue to be measured, the measurement position is a position meeting a reproducibility; and performing a tissue element measurement at the measurement position.

According to the embodiments of the present disclosure, the performing a tissue element measurement at the measurement position includes: performing a plurality of sets of current repeatability tests at the measurement position to determine a current evaluation parameter range; and performing the tissue element measurement at the measurement position in response to the current evaluation parameter range belonging to an expected evaluation parameter range, the expected evaluation parameter range is an evaluation parameter range corresponding to a predetermined state of the measurement position.

According to the embodiments of the present disclosure, the performing a plurality of sets of current repeatability tests at the measurement position to determine a current evaluation parameter range includes: performing the plurality of sets of current repeatability tests at the measurement position to acquire current spectral data of the measurement position corresponding to each current spectral measurement, each set of current repeatability tests includes at least two current spectral measurements; determining, according to each current spectral data corresponding to each set of current repeatability tests, a current evaluation parameter corresponding to each set of current repeatability tests, the current evaluation parameter is configured to evaluate a state of the measurement position; and determining the current evaluation parameter range according to each current evaluation parameter.

According to the embodiments of the present disclosure, the acquiring a target image information of a target position of a tissue to be measured includes: acquiring the target image information of the target position of the tissue to be measured collected by a locating probe.

According to the embodiments of the present disclosure, the acquiring current spectral data of the measurement position corresponding to each current spectral measurement includes: acquiring, in each current spectral measurement, the current spectral data of the measurement position collected by a measurement probe.

According to the embodiments of the present disclosure, the determining the target position as the locating position in response to the target image information being matched with the template image information includes: determining a similarity between the target image information and the template image information; and determining that the target image information is matched with the template image information and determining the target position as the locating position, in response to the similarity being greater than or equal to a similarity threshold.

According to the embodiments of the present disclosure, the determining a similarity between the target image information and the template image information includes: performing a correlation analysis on the target image information and the template image information to obtain a correlation coefficient; and determining the similarity between the target image information and the template image information according to the correlation coefficient.

According to the embodiments of the present disclosure, the internal target image and the internal template image include an OCT image, an MRI image, an ultrasound images, an ECT image or a CT image.

According to the embodiments of the present disclosure, the method further includes: adjusting a position of the locating probe in response to the target image information being not matched with the template image information so as to acquire the target image information of another target position collected by the locating probe, until the target image information is matched with the template image information.

According to the embodiments of the present disclosure, after the determining the target position as the locating position in response to the target image information being matched with the template image information, the method further includes: generating a prompt information configured to prompt that the target position is the locating position, a form of the prompt information includes at least one selected from an image, a voice, or a vibration.

According to another aspect of the present disclosure, an apparatus of measuring tissue element is provided, including: an image information acquisition module configured to acquire a target image information of a target position of a tissue to be measured and a pre-stored template image information of a locating position, the target image information includes a surface target image and/or an internal target image, and the template image information includes a surface template image and/or an internal template image; a locating position determination module configured to determine the target position as the locating position in response to the target image information being matched with the template image information; a measurement position determination module configured to determine a measurement position according to the locating position and a corresponding relationship between the locating position and the measurement position of the tissue to be measured, the measurement position is a position meeting a reproducibility; and a measurement module configured to perform a tissue element measurement at the measurement position.

According to another aspect of the present disclosure, an electronic device is provided, including: one or more processors; a memory configured to store one or more programs; the one or more programs, when executed by the one or more processors, cause the one or more processors to implement the method described above.

According to another aspect of the present disclosure, a system of measuring tissue element is provided, including a locating probe, a measurement probe, and the electronic device described above; the locating probe is configured to collect the target image information of the target position; and the measurement probe is configured to collect current spectral data of the measurement position in each current spectral measurement.

According to the embodiments of the present disclosure, the locating probe and the measurement probe are integrated with each other or separated from each other.

According to the embodiments of the present disclosure, the system further includes a fixation part; a relationship between the fixation part and the locating probe and a relationship between the fixation part and the measurement probe are selected from: the fixation part being configured to fix the locating probe while being separated from the measurement probe; the fixation part being configured to fix the measurement probe while being separated from the locating probe; the fixation part being configured to fix the locating probe and the measurement probe while the locating probe and the measurement probe being fixed at a same position or different positions on the fixation part; or the fixation part being separated from the locating probe and the measurement probe.

According to the embodiments of the present disclosure, a skin status of a skin at the locating position and the measurement position meets a first predetermined condition in a process of fixing the locating probe and the measurement probe to the fixation part.

According to the embodiments of the present disclosure, the fixation part includes a fixation belt and at least one fixation seat; the fixation belt is configured to fix each fixation seat; the fixation seat is configured to fix the locating probe, so that the locating probe is fixed by the fixation part; and the fixation seat is further configured to fix the measurement probe, so that the measurement probe is fixed by the fixation part.

According to the embodiments of the present disclosure, a skin status of a skin at the locating position and the measurement position meets a second predetermined condition in a process of fixing each fixation seat by the fixation belt.

According to the embodiments of the present disclosure, a softness of the fixation belt includes a first softness and a second softness; the first softness is less than the second softness; the first softness is a corresponding softness in the process of fixing each fixation seat by the fixation belt; and the second softness is a corresponding softness after each fixation seat is fixed by the fixation belt.

According to the embodiments of the present disclosure, the fixation belt is a Velcro or an elastic belt.

According to the embodiments of the present disclosure, a surface of the fixation belt is provided with a hole.

According to the embodiments of the present disclosure, a softness of the fixation belt is greater than or equal to a first softness threshold and less than or equal to a second softness threshold.

According to the embodiments of the present disclosure, the system further includes a magnetic part; the fixation belt is entirely or partially a metal hinge, and the magnetic part cooperates with the fixation belt to fix each fixation seat.

According to the embodiments of the present disclosure, the measurement probe does not move in the fixation seat in a process of collecting the current spectral data of the measurement position.

According to the embodiments of the present disclosure, the measurement probe is fixed to the fixation seat in at least one manner selected from: the measurement probe being fixed to the fixation seat by a double-sided adhesive tape; the measurement probe being fixed to the fixation seat by a fastener; the measurement probe being fixed to the fixation seat by a magnetic force; or a friction coefficient between the measurement probe and the fixation seat being greater than or equal to a friction coefficient threshold.

According to another aspect of the present disclosure, a computer-readable storage medium having computer programs stored thereon is provided, the programs, when executed by a processor, implement the method described above.

According to another aspect of the present disclosure, a computer program product containing computer programs is provided, the computer programs, when executed by a processor, implement the method described above.

DETAILED DESCRIPTION OF EMBODIMENTS

Figure 1:
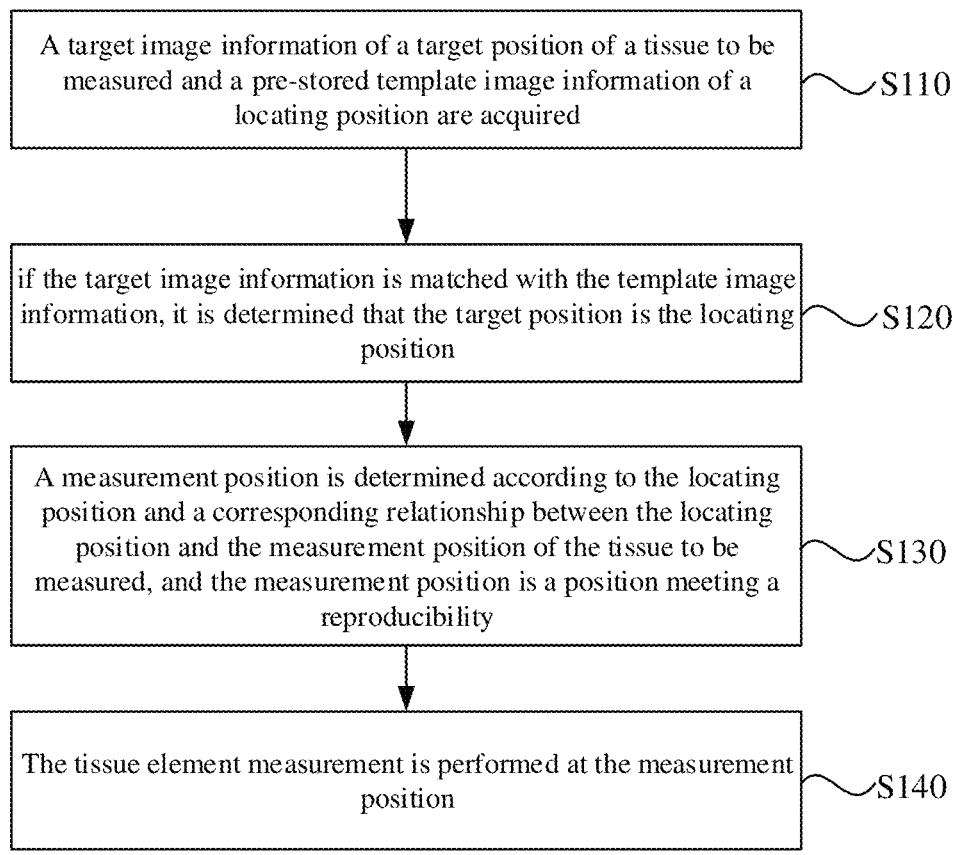
FIG. 1 is a flowchart of a method of measuring tissue element in the embodiments of the present disclosure.

The present disclosure will be further described in detail below in conjunction with the accompanying drawings and the embodiments. It may be understood that the specific embodiments described here are merely for explaining the present disclosure, rather than limiting the present disclosure, and various features recorded in the embodiments may be combined to form a plurality of optional solutions. In addition, it should be noted that, for ease of description, only some structures rather than all structures related to the present disclosure are shown in the accompanying drawings.

For a measurement position, a transmission path of photons is vulnerable to an influence of structural properties and optical properties after the photons enter a tissue, and different measurement regions of an object to be detected or even different measurement positions in a same measurement region correspond to different tissue structures and optical properties. Therefore, if the measurement position determined each time is different, acquired spectral data may be different. However, in order to extract a weak signal, it is required to ensure a reproducibility of a measurement condition, that is, a reproducibility of a measurement position, a measurement temperature and a contact pressure required to be ensured. Ensuring the reproducibility of the measurement position is a basis of achieving the reproducibility of the measurement condition.

That is to say, how to achieve the reproducibility of the measurement position in a tissue element measurement so as to ensure a stable reproduction of the measurement condition has become a primary problem to be solved in the tissue element measurement.

Based on a principle of the tissue element measurement, a near-infrared spectral is generally measured through skin. Therefore, it is required to understand structural properties of the tissue to be measured in order to better understand an influence of the measurement condition on a historical spectral measurement and minimize the above-mentioned influence in the measurement, so as to achieve the reproducibility of the measurement condition.

A skin tissue may be understood as a three-layer skin tissue model based on changes in cellular structure within the skin and blood content with a depth. The three-layer skin tissue includes an epidermis layer, a dermis layer and a subcutaneous fat layer. The epidermis layer has an average thickness of 70 µm to 200 µm, and almost contains no blood flow. The dermis layer has an average thickness of about 0.4 mm to 2.4 mm, and contains a large number of capillaries and a rich blood flow. The subcutaneous fat layer has an average thickness of about 5 mm to 10 mm, and mainly contains medium blood vessels. In the tissue element measurement, a measurement target is generally the dermis layer.

Since the measurement target in the tissue element measurement is the dermis layer and a dermis layer with rich well-circulated blood is conducive to an improvement of a measurement accuracy, it is required that the dermis layer corresponding to the measurement position has a rich and well-circulated blood, that is, the measurement position is a position of the dermis layer with rich and well-circulated blood. In order to achieve the reproducibility of the measurement position and thus ensuring the reproducibility of the measurement condition, it is required to ensure measurement positions determined each time to be consistent. In order to achieve the consistency of the measurement positions determined each time, it is required to accurately determine the measurement position. In order to accurately determine the measurement position, it is possible to accurately determine a locating position corresponding to the measurement position. The locating position corresponding to the measurement position is required to meet the following requirements. First, it is easy to be fixedly measured and has a small individual difference. Second, it has a surface tissue with an obvious texture feature. Third, it has a dermis layer with rich and well-circulated blood. The above-mentioned locating position may have a corresponding relationship with the measurement position, that is, the locating position is the measurement position, or the measurement position is another position having a fixed positional relationship with the locating position. It should be noted that a corresponding relationship between a locating probe and a measurement probe may be determined based on predetermined locating position and measurement position.

In order to determine the locating position, an image matching may be used, that is, a target image information of a target position and a pre-stored template image information of a locating position are acquired, and then the target image information is matched with the template image information to determine whether the target position is the locating position. If it is determined that the target position is the locating position, a measurement position corresponding to the locating position is determined accordingly.

After the measurement position is determined, it is required to perform a tissue element measurement at the measurement position. The tissue element measurement refers to that, a concentration of a tissue element is determined according to acquired current spectral data of a measurement position of a tissue to be measured. The above-mentioned current spectral data of the measurement position is generally collected by a measurement probe. The template image information of the locating position is collected by a locating probe. Fixing of the locating probe and/or the measurement probe is involved in the above processes. Generally, the locating probe and/or the measurement probe are/is fixed using a fixation part, and fixing of the fixation part is involved accordingly. Acquiring the current spectral data may include the following operations: the locating position is determined according to the template image information and the target image information collected by the locating probe. The locating probe and the fixation part are fixed at corresponding positions based on the locating position. The measurement probe is fixed to acquire the current spectral data of the measurement position.

It should be noted that the mentioned above locating probe, the measurement probe, the fixation part themselves and fixing actions may cause a change in the measurement position. This is because gravities of the locating probe, the measurement probe and the fixation part themselves may cause a change in a skin status at a corresponding position, and similarly, a fixing action of fixing the locating probe and/or the measurement probe to the fixation part and a fixing action of fixing the fixation part may also cause a change in the skin status at the corresponding position. The above-mentioned changes in the skin status may lead to a displacement of the measurement probe that is already in a correct position, thus causing a change of the measurement position. The aforementioned changes in the skin status may refer to a skin deformation and/or a change in an internal tissue structure, or the like. In addition, the changes in the skin status (such as skin deformation) at the measurement position caused by the fixing actions may introduce more interference, which may also cause the change of the measurement position. It may be understood that as stated above, the change of the measurement position is caused by the influence of the measurement probe, and thereby a reproducibility of the measurement position is reduced.

In order to achieve the reproducibility of the measurement position, it is required to reduce the influence of the above-mentioned fixing actions on the measurement probe as much as possible. In order to reduce the influence of the fixing actions on the measurement probe, it may be designed from the following three aspects. A first aspect is a positional relationship among the locating probe, the measurement probe and the fixation part. A second aspect is a fixing manner of fixing the locating probe and/or the measurement probe to the fixation part. A third aspect is a fixing manner of the fixation part.

The above-mentioned contents will be described below through specific embodiments.

FIG. 1 is a flowchart of a method of measuring tissue element provided by the embodiments of the present disclosure. The embodiment may be applied to accurately determine a measurement position so as to achieve a reproducibility of the measurement position, and thereby ensuring a reproducibility of the measurement condition. The method may be performed by an apparatus of measuring tissue element, which may be implemented in software and/or hardware. The apparatus may be configured in an electronic device such as a computer and a wearable device, etc. As shown in FIG. 1, the method specifically includes the following operations.

In operation S110, a target image information of a target position of a tissue to be measured and a pre-stored template image information of a locating position are acquired, the target image information includes a surface target image and/or an internal target image, and the template image information includes a surface template image and/or an internal template image.

According to the embodiments of the present disclosure, in order to accurately determine the locating position corresponding to a measurement position, it is possible to acquire the target image information of the target position and the template image information of the locating position, and determine whether the target image information is matched with the template image information so as to determine whether the target position is the locating position. The target image information is an image information of the target position. The template image information is a template image information of the locating position, which may be pre-collected and pre-stored for a subsequent use.

According to the embodiments of the present disclosure, the target image information may include a surface target image and/or an internal target image, and the template image information may include a surface template image and/or an internal template image. The surface target image may refer to an image of a surface with a texture feature of the target position, and the surface template image may refer to an image of a surface with a texture feature of the locating position. The texture feature may include a structural feature composed of textures on a skin surface and an individual feature structure, etc. The individual feature structure may include a birthmark and a mole, etc. The internal template image and the internal target image refer to images that may reflect an internal information of a human body. A dermis layer information may be acquired through the internal template image and the internal target image. Both the internal template image and the internal target image may be internal images acquired based on a medical imaging technology.

For example, the internal template image and the internal target image may include an OCT (Optical Coherence Tomography) image, an MRI (Magnetic Resonance Imaging) image, an ultrasound image, an ECT (Emission Computed Tomography) image, or a CT (Computed Tomography) image. It may be understood that if the target position is consistent with the locating position, the surface target image is matched with the surface template image, and the internal target image is matched with the internal template image. The target image information of the target position may be collected by a locating probe. The template image information of the locating position may be collected by the locating probe, or may not be collected by the locating probe, which may be set according to actual situations and is not limited here.

In operation S120, if the target image information is matched with the template image information, it is determined that the target position is the locating position.

According to the embodiments of the present disclosure, after the target image information and the template image information are acquired, it may be determined whether the target image information is matched with the template image information. If the target image information is matched with the template image information, it may be determined that the target position is the locating position.

Since the target image information includes the surface target image and/or the internal target image, and the template image information includes the surface template image and/or the internal template image, the above-mentioned matching may be understood as that, if the target image information includes the surface target image and the template image information includes the surface template image, the target position may be determined as the locating position in response to a determination that the surface target image is matched with the surface template image.

If the target image information includes the internal target image and the template image information includes the internal template image, it may be determined that the target position is the locating position in response to a determination that the internal target image is matched with the internal template image.

Figure 2:
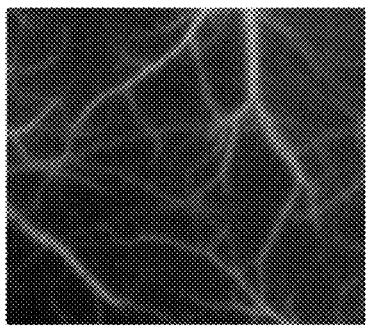
FIG. 2 is a schematic diagram of a template image information of a locating position in the embodiments of the present disclosure.
Figure 3:
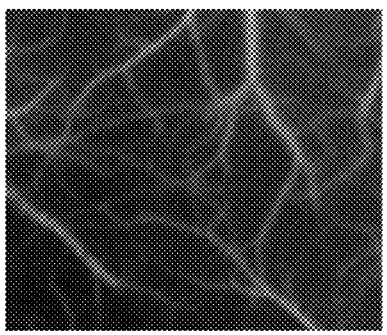
FIG. 3 is a schematic diagram of a target image information of a target position in the embodiments of the present disclosure.

If the target image information includes the surface target image and the internal target image, and the template image information includes the surface template image and the internal template image, then it may be determined that the target position is the locating position in response to a determination that the surface target image is matched with the surface template image and the internal target image is matched with the internal template image. As shown in FIG. 2, a schematic diagram of a template image information of a locating position is given. As shown in FIG. 3, a schematic diagram of a target image information of a target position is given.

According to the embodiments of the present disclosure, whether the target position is the locating position is determined by matching the target image information with the template image information. The target image information includes the surface target image and the internal target image, and the template image information includes the surface template image and the internal template image. In this way, a locating accuracy may be improved.

According to the embodiments of the present disclosure, the template image information includes the surface template image or the internal template image, and the target image information includes the surface target image or the internal target image, so that a matching speed may be improved.

In operation S130, a measurement position is determined according to the locating position and a corresponding relationship between the locating position and the measurement position of the tissue to be measured, and the measurement position is a position meeting a reproducibility.

According to the embodiments of the present disclosure, after the locating position is determined, the measurement position may be determined according to the locating position and the corresponding relationship between the locating position and the measurement position of the tissue to be measured. The measurement position refers to a position at which a tissue element measurement is performed, and the measurement position meets the reproducibility of the measurement position. The locating position has a corresponding relationship with the measurement position, that is, the locating position may be the measurement position, or the measurement position is another position having a fixed positional relationship with the locating position. The so-called fixed positional relationship may be understood as that a distance between the measurement position and the locating position is within a predetermined distance range.

Exemplarily, if the locating position is A, the measurement position may be the locating position A, or another position having a fixed positional relationship with the locating position A, such as position B.

For the measurement position, the reproducibility of the measurement position is met. That is, in each tissue element measurement, if the measurement position is determined using the above-mentioned method, it may be ensured that the measurement position determined in each tissue element measurement remains unchanged. Based on this, the reproducibility of the measurement position may be achieved. Accordingly, the measurement position is a position meeting the reproducibility of the measurement position.

In operation S140, the tissue element measurement is performed at the measurement position.

According to the embodiments of the present disclosure, after the measurement position is determined, the tissue element measurement may be performed at the measurement position. The tissue element measurement refers to that, a concentration of a tissue element is determined according to acquired spectral data of the measurement position of the tissue to be measured.

According to the technical solution of embodiments of the present disclosure, the target image information of the target position and the pre-stored template image information of the locating position are acquired. If the target image information is matched with the template image information, it is determined that the target position is the locating position. The measurement position is determined according to the locating position and the corresponding relationship between the locating position and the measurement position of the tissue to be measured. The tissue element measurement is performed at the measurement position. The measurement position is the position meeting the reproducibility. With the above-mentioned method of comparing image information, the measurement position is accurately determined, and thereby the reproducibility of the measurement position is achieved. On this basis, a reproducibility of a measurement condition may be ensured.

According to the embodiments of the present disclosure, performing the tissue element measurement of the measurement position may include the following operations.

A plurality of sets of current repeatability tests are performed at the measurement position to determine a current evaluation parameter range. If the current evaluation parameter range belongs to an expected evaluation parameter range, the tissue element measurement is performed at the measurement position. The expected evaluation parameter range is an evaluation parameter range corresponding to a predetermined state of the measurement position.

According to the embodiments of the present disclosure, in order to improve a measurement accuracy, it is required to ensure that a condition for performing the tissue element measurement is a predetermined condition. The predetermined state is a state in which the tissue element measurement may be performed. That is, the predetermined state is a state meeting the condition for performing the tissue element measurement. The predetermined evaluation parameter range may be used as a basis for determining whether the state of the measurement position is the predetermined state. In other words, the expected evaluation parameter range may represent an evaluation parameter range corresponding to the predetermined state of the measurement position.

In order to obtain the expected evaluation parameter range that may be used to evaluate whether the measurement condition is in the predetermined state, it is possible to perform a plurality of sets of historical repeatability tests, and each set of historical repeatability tests corresponds to a historical evaluation parameter. The historical repeatability test may mean that a plurality of historical spectral measurements are consecutively performed in a state (for example, fasting state) on a detected object. The repeatability refers to that, a plurality of consecutive measurements are performed on a same detected object and a dispersion of measurement results is analyzed.

According to the embodiments of the present disclosure, the expected evaluation parameter range may be determined as follows. A plurality of sets of historical repeatability tests are performed at the measurement position to acquire historical spectral data of the measurement position corresponding to each historical spectral measurement. Each set of historical repeatability tests includes at least two historical spectral measurements. A historical evaluation parameter corresponding to each set of historical repeatability tests is determined according to each historical spectral data corresponding to each set of historical repeatability tests, and the historical evaluation parameter is used to evaluate the state of the measurement position. The expected evaluation parameter range corresponding to the predetermined state of the measurement position is determined according to each historical evaluation parameter. As stated above, the expected evaluation parameter range corresponding to the measurement position in the predetermined state based on the historical repeatability tests, which provides an evaluation basis for a subsequent tissue element measurement.

According to the embodiments of the present disclosure, a specific form of the historical evaluation parameter may be set according to actual situations and is not limited here. For example, the historical evaluation parameter is CV (Coefficient of Variation). A formula for calculating CV is CV=standard deviation/average value. The smaller the coefficient of variation, the better the reproducibility of the measurement position. The larger the coefficient of variation, the worse the reproducibility of the measurement position.

Before performing the tissue element measurement of the measurement position, it is possible to perform a plurality of sets of current repeatability tests of the measurement position to determine a current evaluation parameter range. The current evaluation parameter range is compared with the expected evaluation parameter range. If the current evaluation parameter range belongs to the expected evaluation parameter range, the tissue element measurement is performed at the measurement position.

According to the embodiments of the present disclosure, the determining the current evaluation parameter range by performing the plurality of sets of current repeatability tests of the measurement position may include the following operations.

The plurality of sets of current repeatability tests are performed at the measurement position to acquire the current spectral data of the measurement position corresponding to each current spectral measurement, and each set of current repeatability tests includes at least two current spectral measurements. The current evaluation parameter corresponding to each set of current repeatability tests is determined according to each current spectral data corresponding to each set of current repeatability tests, and the current evaluation parameter is used to evaluate the state of the measurement position. The current evaluation parameter range is determined according to each current evaluation parameter.

According to the embodiments of the present disclosure, for each set of current repeatability tests, the current spectral data of the measurement position corresponding to each current spectral measurement may be acquired. The current evaluation parameter corresponding to each set of current repeatability tests is determined according to each current spectral data corresponding to each set of current repeatability tests. Each set of current repeatability tests includes at least two current spectral measurements. The above-mentioned operations are repeatedly performed until a predetermined number of tissue element measurements are completed so as to obtain the current evaluation parameter corresponding to each set. The current evaluation parameter range is determined according to each current evaluation parameter.

A specific form of the current evaluation parameter may be set according to actual situations and is not limited here. For example, the current evaluation parameter may be CV.

According to the embodiments of the present disclosure, the acquiring the target image information of the target position of the tissue to be measured may include the following operations.

The target image information of the target position of the tissue to be measured collected by the locating probe is acquired.

Figure 4:
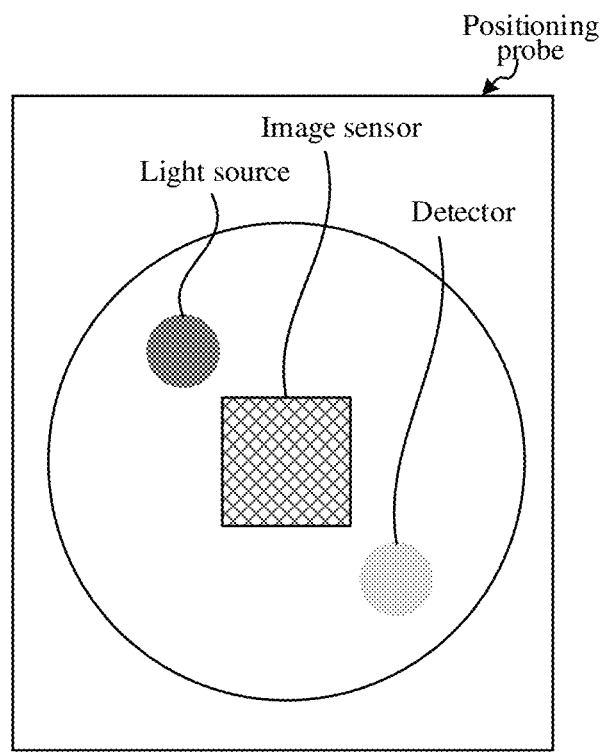
FIG. 4 is a schematic structural diagram of a locating probe in the embodiments of the present disclosure.

According to the embodiments of the present disclosure, the target image information of the target position may be collected by the locating probe. The locating probe may include an image sensor, a light source, and a detector. The image sensor may be used to collect the surface target image of the target position. The detector may be used to collect the internal target image of the target position. As shown in FIG. 4, a schematic structural diagram of a locating probe is given.

According to the embodiments of the present disclosure, acquiring the spectral data of the measurement position corresponding to each current spectral measurement may include the following operations.

In each current spectral measurement, current spectral data of the measurement position collected by a measurement probe is acquired.

Figure 5:
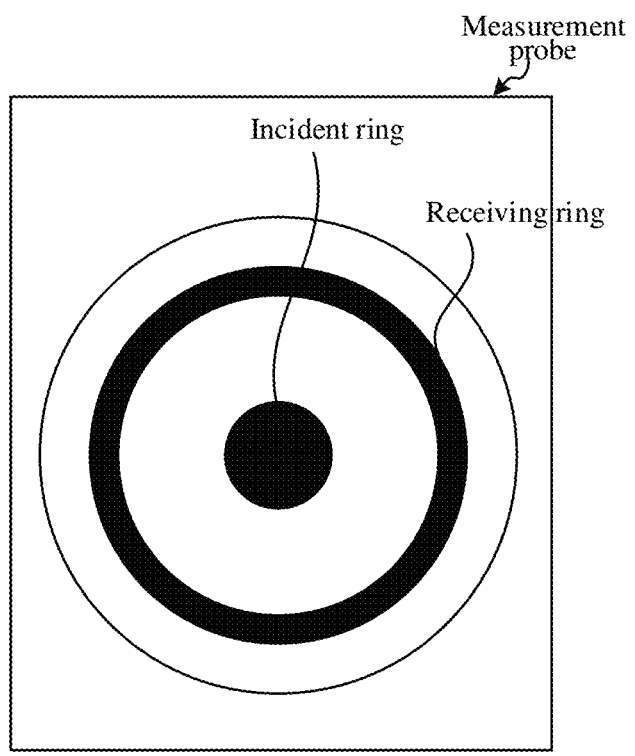
FIG. 5 is a schematic structural diagram of a measurement probe in the embodiments of the present disclosure.

According to the embodiments of the present disclosure, the current spectral data of the measurement position may be collected by the measurement probe. The measurement probe may be a fiber optic probe, which may be designed with multi-ring optical fiber bundles and central incidence, and ring-shaped receiving fiber bundles are provided at different distances from a center of an incident beam to collect the current spectral data of the measurement position. In addition, the historical spectral data of the measurement position may also be collected by the measurement probe. As shown in FIG. 5, a schematic structural diagram of a measurement probe is given.

According to the embodiments of the present disclosure, determining the target position as the locating position in response to the target image information being matched with the template image information may include the following operations.

A similarity between the target image information and the template image information is determined. If the similarity is greater than or equal to a similarity threshold, it is determined that the target image information is matched with the template image information, and the target position is determined as the locating position.

According to the embodiments of the present disclosure, in order to determine whether the target image information is matched with the template image information, it is possible to calculate the similarity between the two and compare whether the similarity is greater than or equal to the similarity threshold. The similarity threshold may be used as a basis for determining whether the target image information is matched with the template image information, that is, if the similarity is greater than or equal to the similarity threshold, it may be determined that the target image information is matched with the template image information, and then it may be determined that the target position is the locating position.

Since the target image information may include the surface target image and/or the internal target image, and the template image information may include the surface template image and/or the internal template image, if the target image information includes the surface target image and the template image information includes the surface template image, the similarity between the surface target image and the surface template image is determined. If the similarity is greater than or equal to the corresponding similarity threshold, it may be determined that the target image information is matched with the template image information.

If the target image information includes the internal target image and the template image information includes the internal template image, the similarity between the internal target image and the internal template image may be determined. If the similarity is greater than or equal to the corresponding similarity threshold, it may be determined that the target image information is matched with the template image information.

If the target image information includes the surface target image and the internal target image, and the template image information includes the surface template image and the internal template image, the similarity between the surface target image and the surface template image and the similarity between the internal target image and the internal template image are determined. If the similarity between the surface target image and the surface template image is greater than or equal to the corresponding similarity threshold, and the similarity between the internal target image and the internal template image is greater than or equal to the corresponding similarity threshold, it may be determined that the target image information is matched with the template image information.

According to the embodiments of the present disclosure, determining the similarity between the target image information and the template image information may include the following operations.

A correlation analysis is performed on the target image information and the template image information to obtain a correlation coefficient. The similarity between the target image information and the template image information are determined according to the correlation coefficient.

According to the embodiments of the present disclosure, in order to determine the similarity between the target image information and the template image information, it is possible to use perform the correlation analysis on the target image information and the template image information, that is, the correlation analysis is performed on the target image information and the template image information to obtain the correlation coefficient, and the similarity between the target image information and the template image information is determined according to the correlation coefficient. In this case, the correlation coefficient may be the similarity.

According to the embodiments of the present disclosure, the internal target image and the internal template image include the OCT image, the MRI image, the ultrasound image, the ECT image or the CT image.

According to the embodiments of the present disclosure, the internal target image and the internal template image may include the OCT image, the MRI image, the ultrasound image, the ECT image or the CT image. OCT is a biomedical imaging technology that integrates low-coherence interference technology, confocal microscope principle and superheterodyne detection technology, and may achieve an internal structure of the detected object. Based on a principle of low-coherent light interference, the OCT technology may accurately acquire an amplitude and a relative phase information of a reflected light by receiving backscattered signals from subtle structural features at different depth positions of a biological tissue, so that an internal structural change of the biological tissue in a depth direction is acquired. Meanwhile, two-dimensional and three-dimensional imaging of the biological tissue may be achieved through a transverse scanning of an OCT scanning probe. According to different imaging theories, the OCT technology may be divided into two categories, including TDOCT (Time Domain Optical Coherence Tomography) and FDOCT (Fourier Domain Optical Coherence Tomography). The internal target image and the target template image described in the embodiments of the present disclosure may be TDOCT images or FDOCT images, which may be set according to actual situations and is not specifically limited here.

According to the embodiments of the present disclosure, the above-mentioned method of measuring tissue element may further include the following operations.

If the target image information is not matched with the template image information, a position of the locating probe is adjusted to acquire the target image information of another target position collected by the locating probe until the target image information is matched with the template image information.

According to the embodiments of the present disclosure, in order to accurately determine the locating position, if the target image information is matched with the template image information, it is possible to adjust the position of the locating probe to collect the target image information of another target position, and determine whether the target image information of the another target position is matched with the pre-stored template image information of the locating position. If it is determined that the target image information is matched with the template image information, it may be determined that the another target position is the locating position. The measurement position is determined according to the locating position and the corresponding relationship between the locating position and the measurement position of the tissue to be measured. The spectral data of the measurement position is acquired, and an expected historical evaluation parameter range of the historical evaluation parameter corresponding to the measurement condition in the predetermined state is determined according to the spectral data. If the target image information is not matched with the template image information, it is possible to continue to adjust the position of the locating probe and perform a matching judgement until the target image information is matched with the template image information. The above-mentioned adjustment method may be manual or automatic.

According to the embodiments of the present disclosure, if the target image information is matched with the template image information, after determining that the target position is the locating position, the method may further include: a prompt information for prompting that the target position is the locating position is generated. A form of the prompt information includes at least one selected from an image, a voice or a vibration.

According to the embodiments of the present disclosure, in order to enable a user to know in time whether the target position is the locating position, the prompt information may be generated after the target position is determined as the locating position. The prompt information may be used to prompt that the target position is the locating position. The specific form of the prompt information may include at least one selected from an image, a voice or a vibration.

Figure 6:
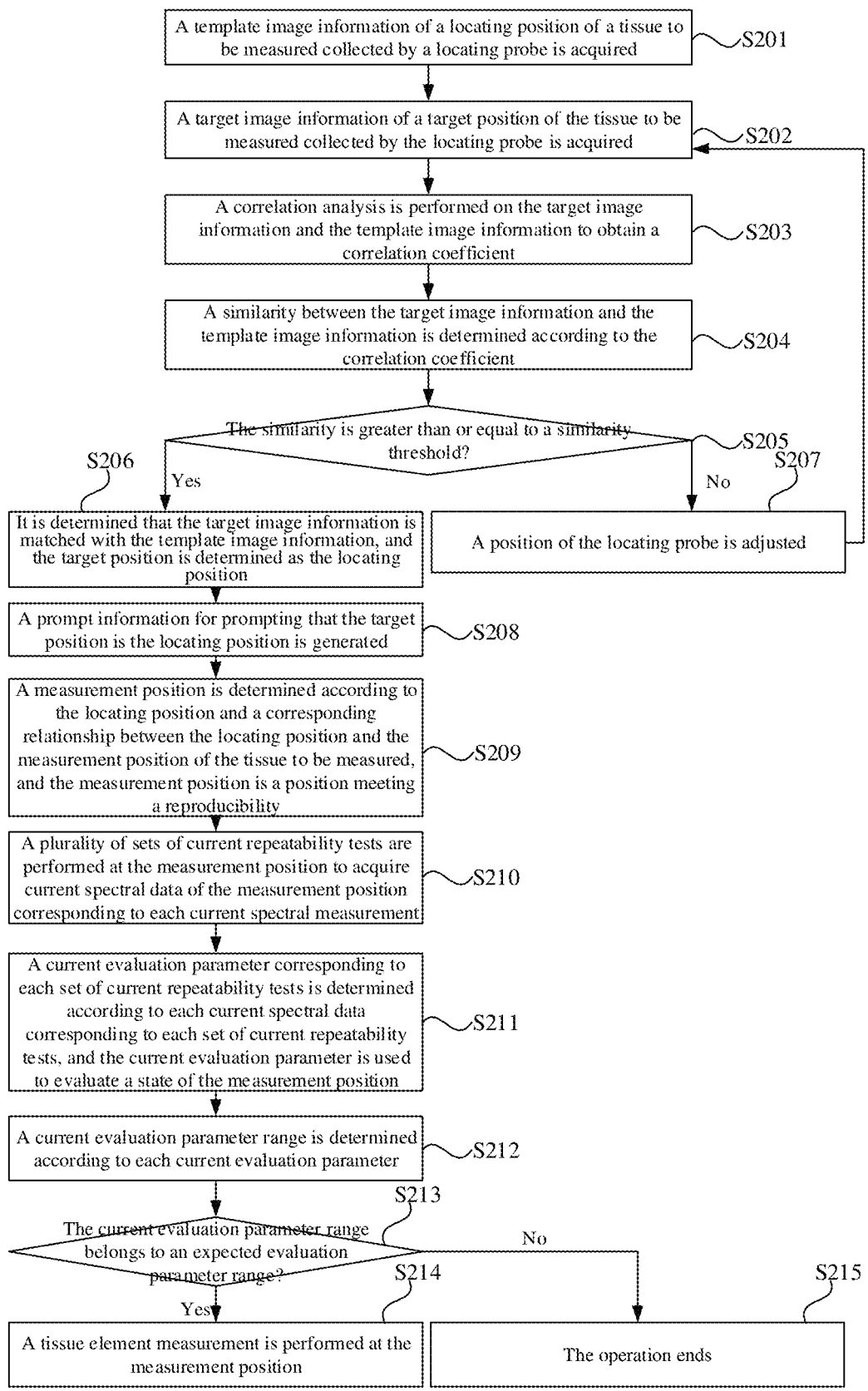
FIG. 6 is a flowchart of another method of measuring tissue element in the embodiments of the present disclosure.

FIG. 6 is a flowchart of another method of measuring tissue element provided by the embodiments of the present disclosure. The embodiment may be applied to accurately determine a measurement position so as to achieve a reproducibility of the measurement position, and thereby ensuring a reproducibility of the measurement condition. The method may be performed by an apparatus of measuring tissue element, which may be implemented in software and/or hardware. The apparatus may be configured in an electronic device such as a computer and a wearable device, etc. As shown in FIG. 6, the method specifically includes the following operations.

In operation S201, a template image information of a locating position of a tissue to be measured collected by a locating probe is acquired.

In operation S202, a target image information of a target position of the tissue to be measured collected by the locating probe is acquired.

According to the embodiments of the present disclosure, the target image information includes a surface target image and/or an internal target image, and the template image information includes a surface template image and/or an internal template image. The internal target image and the internal template image include an OCT image, an MRI image, an ultrasound image, an ECT image or a CT image. The locating probe includes an image sensor, a light source, and a detector.

In operation S203, a correlation analysis is performed on the target image information and the template image information to obtain a correlation coefficient.

In operation S204, a similarity between the target image information and the template image information is determined according to the correlation coefficient.

In operation S205, it is determined whether the similarity is greater than or equal to a similarity threshold; if yes, operation S206 is performed; if no, operation S207 is performed.

In operation S206, it is determined that the target image information is matched with the template image information, and the target position is determined as the locating position, and operation S208 is performed.

In operation S207, a position of the locating probe is adjusted, and operation S202 is performed.

In operation S208, a prompt information for prompting that the target position is the locating position is generated.

According to the embodiments of the present disclosure, a form of the prompt information includes at least one selected from an image, a voice or a vibration.

In operation S209, a measurement position is determined according to the locating position and a corresponding relationship between the locating position and the measurement position of the tissue to be measured, and the measurement position is a position meeting a reproducibility.

In operation S210, a plurality of sets of current repeatability tests are performed at the measurement position to acquire current spectral data of the measurement position corresponding to each current spectral measurement.

According to the embodiments of the present disclosure, each set of current repeatability tests includes at least two current spectral measurements.

In operation S211, a current evaluation parameter corresponding to each set of current repeatability tests is determined according to each current spectral data corresponding to each set of current repeatability tests, and the current evaluation parameter is used to evaluate a state of the measurement position.

In operation S212, a current evaluation parameter range is determined according to each current evaluation parameter.

In operation S213, it is determined whether the current evaluation parameter range belongs to an expected evaluation parameter range, and the expected evaluation parameter range is an evaluation parameter range corresponding to a predetermined state of the measurement position; if yes, operation S214 is performed; if no, operation S215 is performed.

In operation S214, a tissue element measurement is performed at the measurement position.

In operation S215, the operation ends.

According to the embodiments of the present disclosure, an execution order of operation S208 and operations S209 to S215 may be set according to actual situations, and is not limited here.

In order to determine an influence of the technical solution provided by the embodiments of the present disclosure on the reproducibility of the measurement position, a historical repeatability test is performed, in which a historical evaluation parameter is CV.

According to the embodiments of the present disclosure, a set of historical repeatability tests are performed under a fasting condition. The light source has wavelengths of 1040 nm, 1230 nm, 1320 nm, 1550 nm and 1600 nm. A position on a forearm extensor side of an object to be detected is selected as the measurement position, and another position on the forearm extensor side is selected as the locating position. Each coefficient of variation is determined by using the technical solution provided by the embodiments of the present disclosure (referred to as a locating solution), and each historical spectral data of the measurement position is directly acquired and each coefficient of variation is determined according to each historical spectral data by not using the technical solution provided by the embodiments of the present disclosure (referred to as a non-locating solution). Each coefficient of variation corresponding to the locating solution is set as $CV_1(\lambda)$, and each coefficient of variation corresponding to the non-locating solution is set as $CV_2(\lambda)$, $\lambda$ is 1040 nm, 1230 nm, 1320 nm, 1550 nm or 1600 nm.

For the locating solution, in operation a, the template image information of the locating position collected by the locating probe is acquired and stored. In operation b, for each historical spectral measurement, the target image information of the target position collected by the locating probe is acquired. In operation c, the target position is determined as the locating position in response to a determination that the target image information is matched with the template image information. In operation d, the measurement position is determined according to the locating position and the corresponding relationship between the locating position and the measurement position of the tissue to be measured.

In operation e, for each wavelength, historical spectral data of the measurement position is acquired. In operation f, the coefficient of variation $CV_1(\lambda)$ corresponding to each wavelength is determined according to the historical spectral data corresponding to each wavelength. The above-mentioned operation b to operation f are repeatedly performed until a predetermined number of historical spectral measurements are completed to obtain the corresponding coefficients of variation. Each coefficient of variation obtained by the locating solution is shown in Table 1 below. As shown in Table 1, a table of coefficient of variation is given.

For the non-locating solution, for each historical spectral measurement, the historical spectral data of the measurement position at each wavelength is directly acquired. The coefficient of variation $CV_2(\lambda)$ corresponding to each wavelength is determined according to the historical spectral data corresponding to each wavelength. Each coefficient of variation obtained by the non-locating solution is shown in Table 1.

TABLE 1

| | Wavelength (nm) | | | | | |
|---|---|---|---|---|---|---|
| | 1040 | 1230 | 1320 | 1320 | 1550 | 1600 |
| $CV_1(\lambda)$ | 0.00283 | 0.00348 | 0.00376 | 0.00501 | 0.00440 | 0.00507 |
| $CV_2(\lambda)$ | 0.11036 | 0.15343 | 0.17019 | 0.26085 | 0.25297 | 0.29413 |

As shown in Table 1, the coefficient of variation obtained by using the locating solution is between 0.0028 and 0.0051, and the coefficient of variation obtained by using the non-locating solution is between 0.110 and 0.2942. Therefore, by adopting the locating technical solutions provided by the embodiments of the present disclosure, the reproducibility of the measurement position may be significantly improved.

According to the technical solutions of embodiments of the present disclosure, by comparing the image information, the measurement position is accurately determined, and thereby the reproducibility of the measurement position is achieved. On this basis, the reproducibility of the measurement condition is ensured. In addition, an expected historical evaluation parameter range of the historical evaluation parameter corresponding to the measurement position in the predetermined state is determined based on the historical repeatability test, which provides an evaluation basis for a subsequent tissue element measurement.

Figure 7:
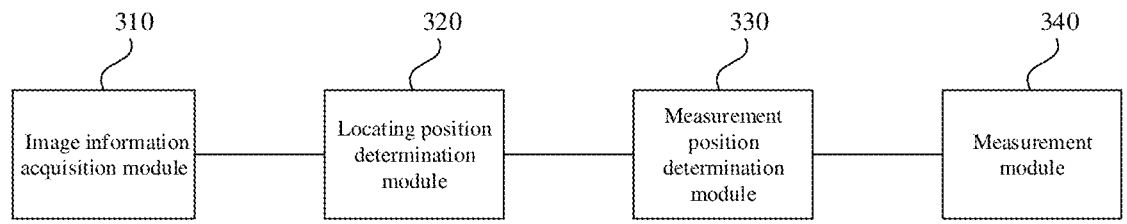
FIG. 7 is a schematic structural diagram of an apparatus of measuring tissue element in the embodiments of the present disclosure.

FIG. 7 is a schematic structural diagram of an apparatus of measuring tissue element provided by the embodiments of the present disclosure. The embodiment may be applied to accurately determine a measurement position so as to achieve a reproducibility of the measurement position, and thereby ensuring a reproducibility of the measurement condition. The apparatus may be implemented in software and/or hardware, and the apparatus may be configured in an electronic device such as a computer and a wearable device, etc.

As shown in FIG. 7, the apparatus may include an image information acquisition module 310, a locating position determination module 320, a measurement position determination module 330, and a measurement module 340.

The image information acquisition module 310 is configured to acquire a target image information of a target position of a tissue to be measured and a pre-stored template image information of a locating position. The target image information includes a surface target image and/or an internal target image, and the template image information includes a surface template image and/or an internal template image.

The locating position determination module 320 is configured to determine the target position as the locating position in response to the target image information being matched with the template image information.

The measurement position determining module 330 is configured to determine a measurement position according to the locating position and a corresponding relationship between the locating position and the measurement position of the tissue to be measured, and the measurement position is a position meeting a reproducibility.

The measurement module 340 is configured to perform a tissue element measurement at the measurement position.

According to the technical solution of the embodiments of the present disclosure, the target image information of the target position and the pre-stored template image information of the locating position are acquired. The target position is determined as the locating position in response to the target image information being matched with the template image information. The measurement position is determined according to the locating position and the corresponding relationship between the locating position and the measurement position of the tissue to be measured. The tissue element measurement is performed at the measurement position, and the measurement position is the position meeting the reproducibility. As stated above, by comparing the image information, the measurement position is accurately determined, and thereby the reproducibility of the measurement position is achieved. On this basis, the reproducibility of the measurement condition is ensured.

According to the embodiments of the present disclosure, the measurement module 340 may include a current evaluation parameter range determination sub-module and a measurement sub-module.

The current evaluation parameter range determination sub-module is configured to perform a plurality of sets of current repeatability tests at the measurement position to determine a current evaluation parameter range.

The measurement sub-module is configured to perform a tissue element measurement at the measurement position in response to the current evaluation parameter range belonging to an expected evaluation parameter range, and the expected evaluation parameter range is an evaluation parameter range corresponding to a predetermined state of the measurement position.

According to the embodiments of the present disclosure, the current evaluation parameter range determination sub-module may include a current spectral data acquisition unit, a current evaluation parameter determination unit and a current evaluation parameter range determination unit.

The current spectral data acquisition unit is configured to perform a plurality of sets of current repeatability tests at the measurement position to acquire current spectral data of the measurement position corresponding to each current spectral measurement, and each set of current repeatability tests includes at least two current spectral measurements.

The current evaluation parameter determination unit is configured to determine a current evaluation parameter corresponding to each set of current repeatability tests according to each current spectral data corresponding to each set of current repeatability tests, and the current evaluation parameter is used to evaluate the state of the measurement position.

The current evaluation parameter range determination unit is configured to determine the current evaluation parameter range according to each current evaluation parameter.

According to the embodiments of the present disclosure, acquiring the target image information of the target position of the tissue to be measured may include the following operations.

The target image information of the target position of the tissue to be measured collected by a locating probe is acquired.

According to the embodiments of the present disclosure, the current spectral data acquisition unit may include a current spectral data acquisition sub-unit.

The current spectral data acquisition sub-unit is configured to acquire current spectral data of the measurement position collected by a measurement probe in each current spectral measurement.

According to the embodiments of the present disclosure, the locating position determination module 320 may include a similarity determination sub-module and a locating position determination sub-module.

The similarity determination sub-module is configured to determine a similarity between the target image information and the template image information.

The locating position determination sub-module is configured to determine that the target image information is matched with the template image information and determine the target position as the locating position in response to the similarity being greater than or equal to a similarity threshold.

According to the embodiments of the present disclosure, the similarity determination sub-module may include a correlation coefficient determination unit and a similarity determination unit.

The correlation coefficient determination unit is configured to perform a correlation analysis on the target image information and the template image information to obtain a correlation coefficient.

The similarity determination unit is configured to determine the similarity between the target image information and the template image information according to the correlation coefficient.

According to the embodiments of the present disclosure, the internal target image and the internal template image include an OCT image, an MRI image, an ultrasound image, an ECT image or a CT image.

According to the embodiments of the present disclosure, the above-mentioned apparatus of measuring tissue element may further include an adjustment module.

The adjustment module is configured to adjust a position of the locating probe in response to the target image information being not matched with the template image information, so as to acquire the target image information of another target position collected by the locating probe until the target image information is matched with the template image information.

According to the embodiments of the present disclosure, the above-mentioned apparatus of measuring tissue element may further include a prompt information generation module.

The prompt information generation module is configured to generate a prompt information for prompting that the target position is the locating position, and a form of the prompt information includes at least one selected from an image, a voice or a vibration.

The apparatus of measuring tissue element configured in an electronic device provided by the embodiments of the present disclosure may be used to perform the method of measuring tissue element applied to the electronic device provided by any embodiment of the present disclosure, and the apparatus has corresponding functional modules and beneficial effects for performing the method.

Figure 8:
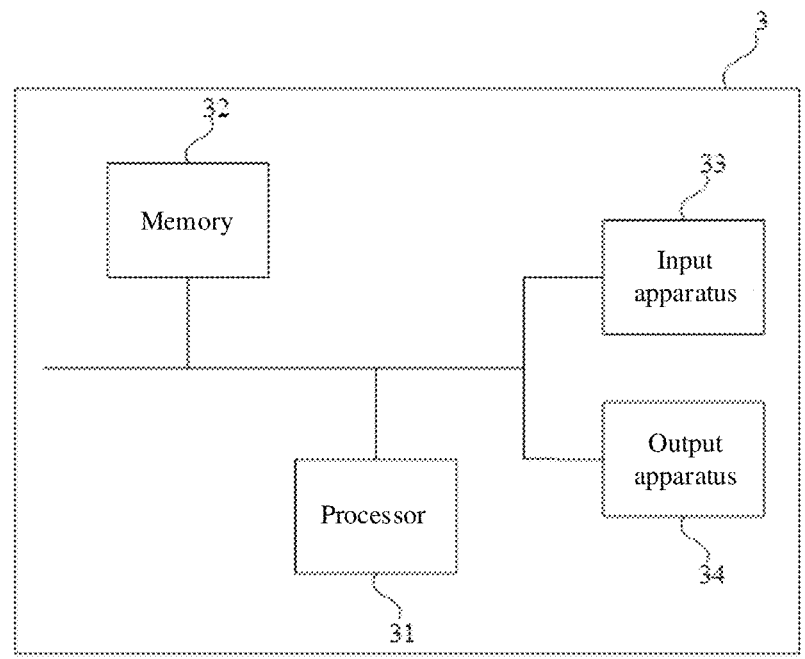
FIG. 8 is a schematic structural diagram of an electronic device in the embodiments of the present disclosure.

FIG. 8 is a schematic structural diagram of an electronic device provided by the embodiments of the present disclosure. An electronic device 3 shown in FIG. 8 is merely an example, which should not bring any limitations on functions and the application scope of the embodiments of the present disclosure. As shown in FIG. 8, the electronic device 3 provided by the embodiments of the present disclosure includes a processor 31, a memory 32, an input apparatus 33, and an output apparatus 34. The electronic device 3 may include one or more processors 31, and FIG. 8 shows one processor 31 as an example. The processor 31, the memory 32, the input apparatus 33 and the output apparatus 34 in the electronic device 3 may be connected through a bus or in other manners, and FIG. 8 shows a connection through a bus as an example.

The memory 32 is a computer-readable storage medium, and may be used to store software programs, computer-executable programs and modules, such as program instructions/modules corresponding to the method of measuring tissue element (e.g., the image information acquisition module 310, the locating position determination module 320, the measurement position determination module 330 and the measurement module 340 in the apparatus of measuring tissue element) in the embodiments of the present disclosure. The processor 31 may execute various functional applications and data processing by executing software programs, instructions and modules stored in the memory 32, thereby implementing the method of measuring tissue element applied to the electronic device 3 provided by the embodiments of the present disclosure.

The memory 32 may mainly include a program storage area and a data storage area. The program storage area may store an operating system and an application program required by at least one function. The data storage area may store data etc. generated by using the electronic device 3. In addition, the memory 32 may include a high-speed random access memory, and may further include a non-transitory memory, such as at least one magnetic disk storage device, a flash memory device, or other non-transitory solid-state storage devices. In some embodiments, the memory 32 may further include a memory provided remotely with respect to the processor 31, and such remote memory may be connected to the electronic device 3 through a network. Examples of the above-mentioned network include, but are not limited to, the Internet, intranet, local area network, mobile communication network and a combination thereof.

The input apparatus 33 may be configured to receive a numeric or character information input by a user so as to generate a key signal input related to user settings and function control of the electronic device. The output apparatus 34 may include a display electronic device such as a display screen, etc.

Certainly, those skilled in the art may understand that the processor may also implement the technical solution of the method of measuring tissue element applied to the electronic device provided by any embodiment of the present disclosure. For the hardware structure and functions of the electronic device, reference may be made to the content explanation of the embodiments.

Figure 9:
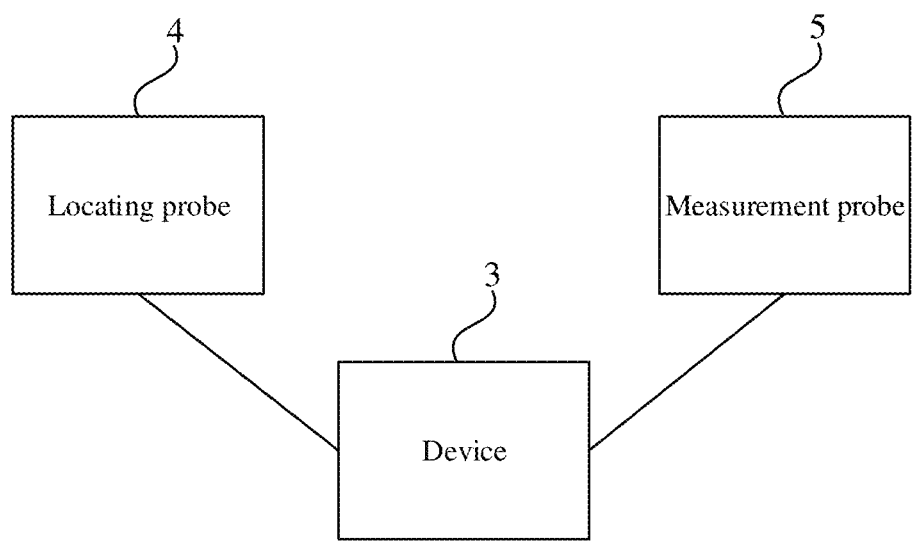
FIG. 9 is a schematic structural diagram of a system of measuring tissue element in the embodiments of the present disclosure.

FIG. 9 is a schematic structural diagram of a system of measuring tissue element provided by the embodiments of the present disclosure. The embodiment may be applied to accurately determine a measurement position so as to achieve a reproducibility of the measurement position, and thereby ensuring a reproducibility of the measurement condition. As shown in FIG. 9, the system of measuring tissue element may include the electronic device 3 described in the embodiments of the present disclosure, a locating probe 4 and a measurement probe 5. The electronic device 3 may include the apparatus of measuring tissue element described in the embodiments of the present disclosure. A structure and a working principle of the system will be described below in conjunction with the accompanying drawings.

The locating probe 4 is configured to collect the target image information of the target position.

The measurement probe 5 is configured to collect the current spectral data of the measurement position in each current spectral measurement.

In the embodiments of the present disclosure, for specific processing processes of the electronic device 3, the locating probe 4 and the measurement probe 5, reference may be made to the above-mentioned descriptions of sections corresponding to the method of measuring tissue element, and details will not be repeated here.

According to the technical solutions of embodiments of the present disclosure, by comparing the image information, the electronic device accurately determines the measurement position and thereby achieving the reproducibility of the measurement position. On this basis, the reproducibility of the measurement condition is ensured.

Figure 10:
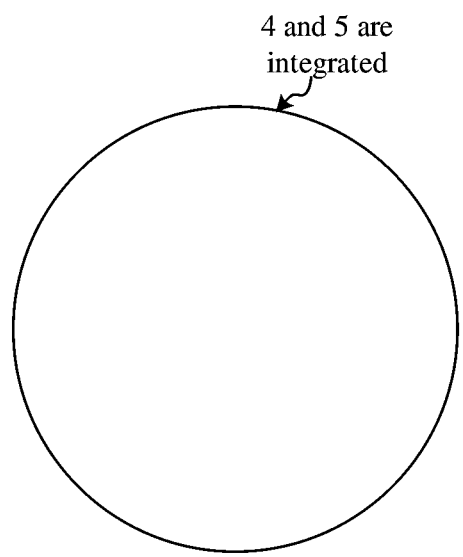
FIG. 10 is a schematic diagram of a locating probe and a measurement probe in the embodiments of the present disclosure.
Figure 11:
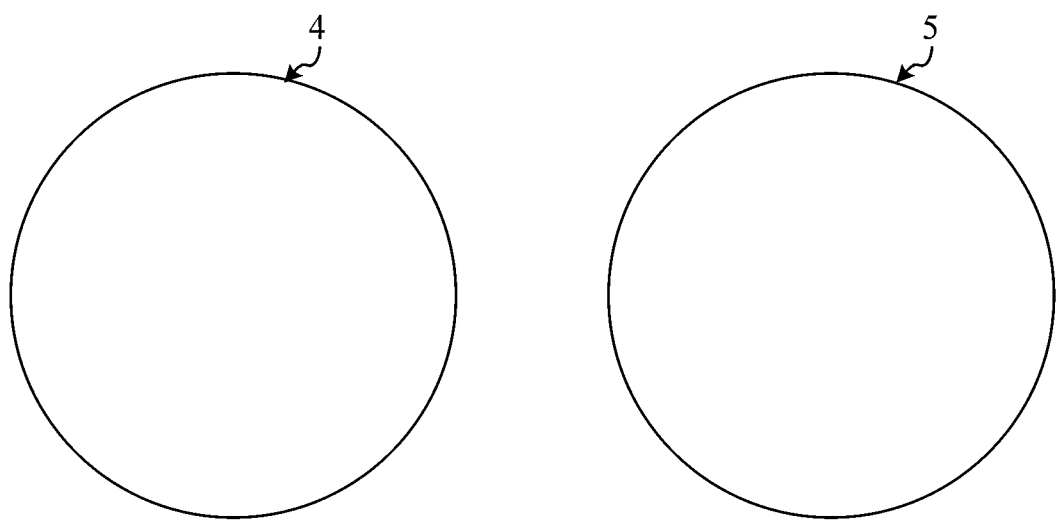
FIG. 11 is another schematic diagram of a locating probe and a measurement probe in the embodiments of the present disclosure.

According to the embodiments of the present disclosure, as shown in FIG. 10 and FIG. 11, the locating probe 4 and the measurement probe 5 are integrated or separated.

According to the embodiments of the present disclosure, as shown in FIG. 10, a schematic diagram of a locating probe and a measurement probe is provided. In FIG. 10, the locating probe 4 and the measurement probe 5 are integrated, that is, the integrated locating probe 4 and the measurement probe 5 may be configured to collect the target image information and the template image information, and may also be configured to collect the spectral data. As shown in FIG. 11, another schematic diagram of the locating probe and the measurement probe is given. In FIG. 11, the locating probe 4 is separated from the measurement probe 5. That is, the locating probe and the measurement probe are two independent probes.

According to the embodiments of the present disclosure, as shown in FIG. 12 to FIG. 19, the above-mentioned system of measuring tissue element may further include a fixation part 6. A relationship between the fixation part 6 and the locating probe 4 and a relationship between the fixation part 6 the measurement probe 5 may be one selected from: the fixation part 6 being used to fix the locating probe 4 and being separated from the measurement probe 5; the fixation part 6 being used to fix the measurement probe 5 and being separated from the locating probe 4; the fixation part 6 being used to fix the locating probe 4 and the measurement probe 5, and the locating probe 4 and the measurement probe 5 being fixed at a same position or different positions on the fixation part 6; or the fixation part 6 being separated from both the locating probe 4 and the measurement probe 5.

According to the embodiments of the present disclosure, after the target position is determined as the locating position, that is, after the locating of the locating position is completed, the locating probe 4 may be fixed, and a position corresponding to the locating probe 4 is the locating position. Accordingly, as the determination of the locating position, the measurement position corresponding to the locating position may also be determined. After the locating probe 4 is fixed, a position of the measurement probe 5 having a fixed positional relationship with the locating probe 4 is also determined. At this time, the position corresponding to the measurement probe 5 is the measurement position. The locating probe 4 and/or the measurement probe 5 may be fixed to the fixation part 6. According to whether the measurement position is the same as the locating position and whether the measurement probe 5 is fixed to the fixation part 6, the positional relationship between the locating probe 4 and the fixation part 6 and the positional relationship between the measurement probe 5 and the fixation part 6 may include four cases, which will be specifically described below with reference to the accompanying drawings.

Figure 12:
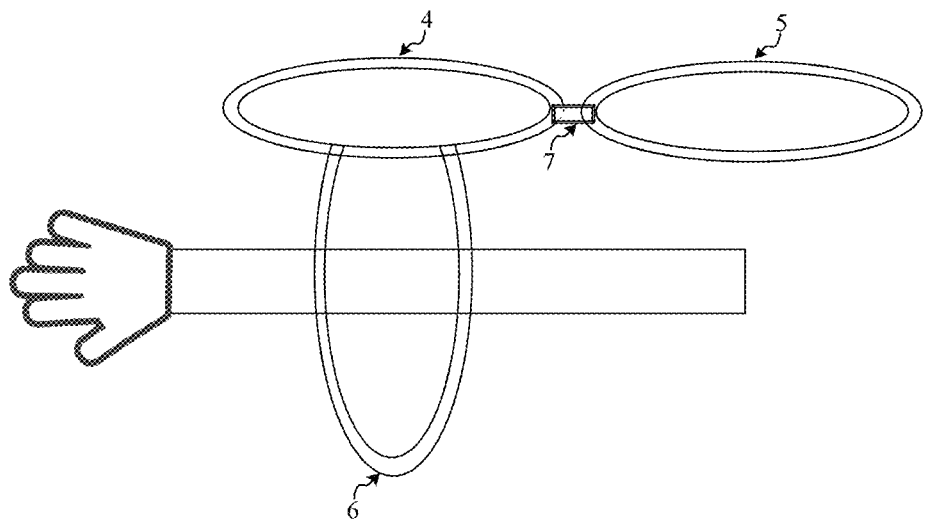
FIG. 12 is a schematic diagram of a positional relationship between a probe and a fixation part in the embodiments of the present disclosure.

In a first case, the locating probe 4 is fixed to the fixation part 6 and the measurement probe 5 is separated from the fixation part 6. This case refers to that the measurement position is different from the locating position, and the measurement probe 5 is not fixed to the fixation part 6. The separation may mean that the two are connected by a connector, and the two mentioned here refer to the measurement probe 5 and the fixation part 6. Since the locating probe 4 and the measurement probe 5 are arranged at different positions, it may be drawn that the measurement position is different from the locating position, as shown in FIG. 12. As shown in FIG. 12, a schematic diagram of a positional relationship between a probe and the fixation part is given. In FIG. 12, the measurement probe 5 is separated from the fixation part 6 and is connected to the fixation part 6 through a connector 7. Before the locating is completed, the measurement probe 5 may be located on the locating probe 4. After the locating is completed, that is, after the target position is determined as the locating position, the measurement probe 5 may be flipped to a position parallel to the locating probe 4 and close to a skin at the measurement position. According to the embodiments of the present disclosure, since the locating probe 4 is fixed to the fixation part 6 and the measurement probe 5 is separated from the fixation part 6, the locating probe 4 and the measurement probe 5 are arranged at different positions. The locating probe 4 is arranged at a position corresponding to the locating position, and the measurement probe 5 is arranged at a position corresponding to the measurement position. Therefore, it may be drawn that the measurement position is different from the locating position. Based on this, in this case, it is possible to acquire the spectral data of another position (i.e., the measurement position) having a specific fixed positional relationship with the locating position.

Figure 13:
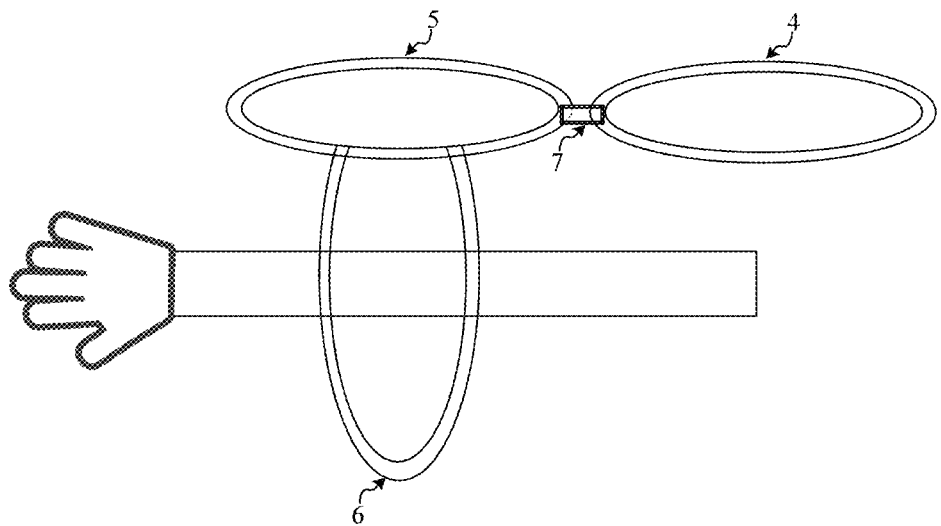
FIG. 13 is a schematic diagram of another positional relationship between a probe and a fixation part in the embodiments of the present disclosure.

In a second case, the measurement probe 5 is fixed to the fixation part 6, and the locating probe 4 is separated from the fixation part 6, as shown in FIG. 13. The separation may mean that the locating probe 4 and the fixation part 5 are connected through the connector 7. As shown in FIG. 13, a schematic diagram of another positional relationship between the probe and the fixation part is given. In FIG. 13, the locating probe 4 is separated from the fixation part 6 and is connected to the fixation part 6 through the connector 7.

Figure 14:
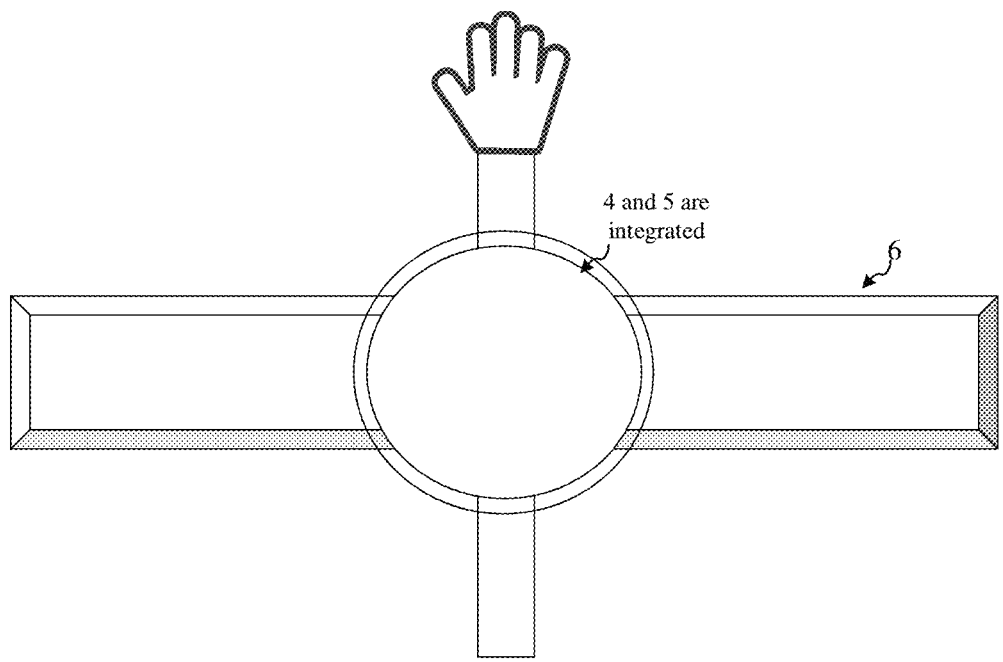
FIG. 14 is a schematic diagram of another positional relationship between a probe and a fixation part in the embodiments of the present disclosure.
Figure 15:
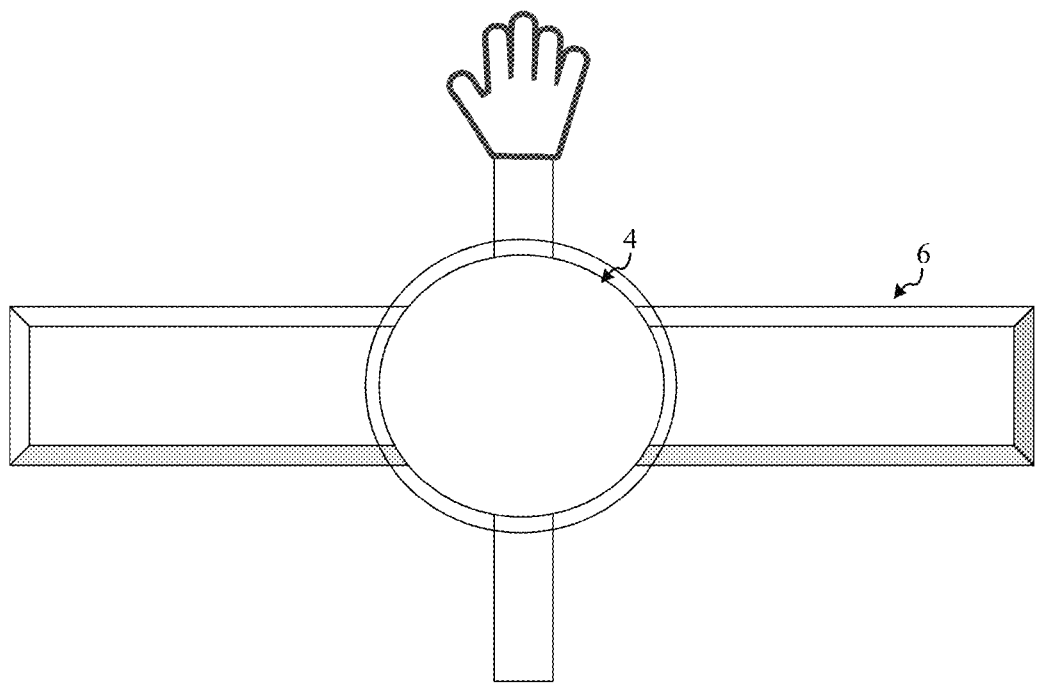
FIG. 15 is a schematic diagram of another positional relationship between a probe and a fixation part in the embodiments of the present disclosure.
Figure 16:
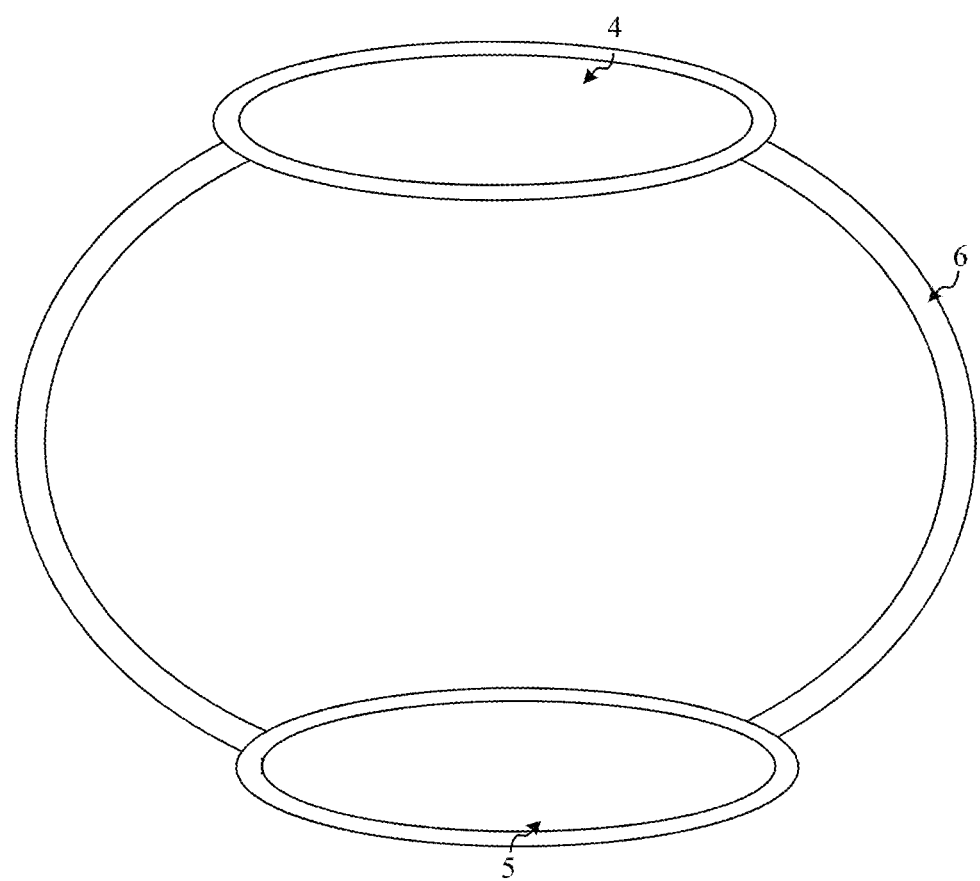
FIG. 16 is a schematic diagram of another positional relationship between a probe and a fixation part in the embodiments of the present disclosure.

In a third case, the locating probe 4 and the measurement probe 5 are fixed at a same position or different positions on the fixation part 6. In this case, the locating probe 4 and the measurement probe 5 may be integrated or separated, as shown in FIG. 14 to FIG. 16. As shown in FIG. 14, a schematic diagram of another positional relationship between the probe and the fixation part is given. In FIG. 14, the locating probe 4 and the measurement probe 5 are integrated. The measurement position described above may be the same as the locating position, or may be different from the locating position. In order to acquire the spectral data of the measurement position different from the locating position, the integrated locating probe 4 and the measurement probe 5 may be adjusted to another position after the locating of the locating position is completed. As shown in FIG. 15, a schematic diagram of another positional relationship between the probe and the fixation part is given. In FIG. 15, the locating probe 4 and the measurement probe 5 are separated, and the locating probe 4 and the measurement probe 5 are fixed at the same position on the fixation part 6. The measurement probe 5 is not shown in FIG. 15. The locating probe 4 and the measurement probe 5 may respectively collect the image information and the spectral data by flipping. As shown in FIG. 16, a schematic diagram of another positional relationship between the probe and the fixation part is given. In FIG. 16, the locating probe 4 and the measurement probe 5 are separated, and the locating probe 4 and the measurement probe 5 are fixed at different positions on the fixation part 6. According to the embodiments of the present disclosure, since the locating probe 4 and the measurement probe 5 are arranged at different positions of the fixation part 6, the locating probe 4 is arranged at a position corresponding to the locating position, and the measurement probe 6 is arranged at a position corresponding to the measurement position, it may be drawn that the measurement position is different from the locating position. Based on this, in the case shown in FIG. 16, it is possible to acquire the spectral data at another position (i.e., the measurement position) having a specific fixed positional relationship with the locating position.

Figure 17:
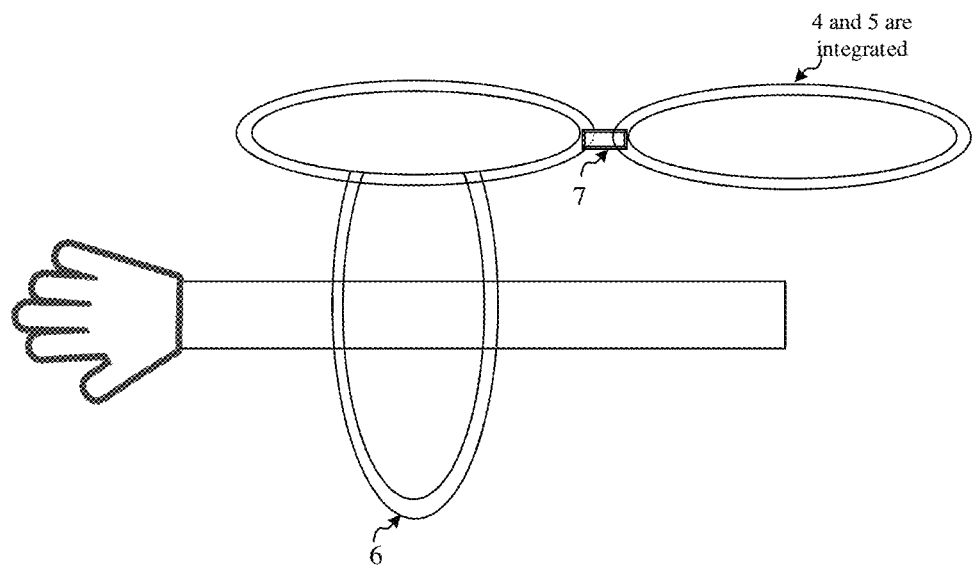
FIG. 17 is a schematic diagram of another positional relationship between a probe and a fixation part in the embodiments of the present disclosure.
Figure 18:
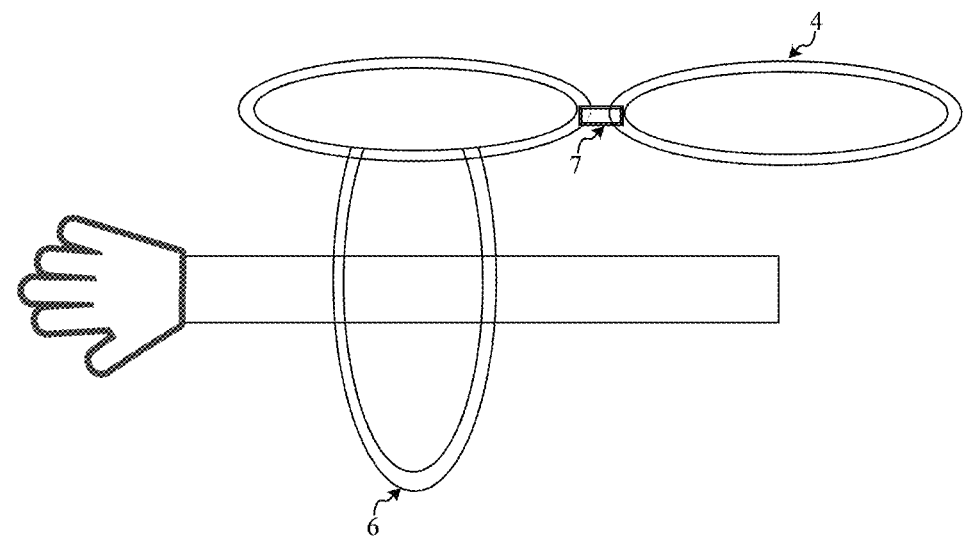
FIG. 18 is a schematic diagram of another positional relationship between a probe and a fixation part in the embodiments of the present disclosure.
Figure 19:
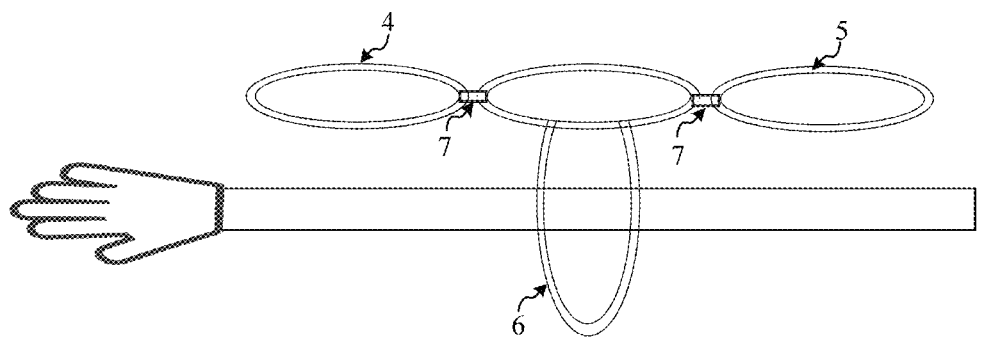
FIG. 19 is a schematic diagram of another positional relationship between a probe and a fixation part in the embodiments of the present disclosure.

In a fourth case, the locating probe 4 and the measurement probe 5 are separated from the fixation part 6. The separation may mean that the fixation part 6 is connected to the locating probe 4 through the connector 7, and the fixation part 6 is connected to the measurement probe 5 through the connector 7. The locating probe 4 and the measurement probe 5 may be integrated or separated, as shown in FIG. 17 to FIG. 19. As shown in FIG. 17, a schematic diagram of another positional relationship between the probe and the fixation part is given. In FIG. 17, the locating probe 4 and the measurement probe 5 are integrated. As shown in FIG. 18, a schematic diagram of another positional relationship between the probe and the fixation part is given. In FIG. 18, the locating probe 4 and the measurement probe 5 are separated, and the locating probe 4 and the measurement probe 5 are located at the same position. The measurement probe 5 is not shown in FIG. 18. The locating probe 4 and the measurement probe 5 may respectively collect the image information and the spectral data by flipping. As shown in FIG. 19, a schematic diagram of another positional relationship between the probe and the fixation part is given. In FIG. 19, the locating probe 4 and the measurement probe 5 are separated, and the locating probe 4 and the measurement probe 5 are located at different positions.

According to the embodiments of the present disclosure, since a fixing action of fixing the locating probe 4 and/or the measurement probe 5 to the fixation part 6 and a fixing action of fixing the fixation part 6 may affect the measurement probe 5 and thereby affecting the reproducibility of the measurement position, it is required to reduce the influence of the fixing actions on the measurement probe 5 as much as possible in order to achieve the reproducibility of the measurement position, which may be specifically designed from the following two aspects. In a first aspect, the measurement probe 5 and the locating probe 4 are located at different positions. In a second aspect, the measurement probe 5 is separated from the fixation part 6. The above-mentioned two aspects of design may be implemented simultaneously, or one of them may be implemented. The simultaneous implementation of the above-mentioned two aspects of design may minimize the influence on the measurement probe 5.

For the above-mentioned four cases, in the first case and the fourth case, the locating probe 4 and the measurement probe 5 are separated from the fixation part 6, the locating probe 4 and the measurement probe 5 are located at different positions, the reproducibility of the measurement position is achieved by fixing the measurement probe 5 and the locating probe 4 at different positions and separating the measurement probe 5 from the fixation part 6. In the third case, the locating probe 4 and the measurement probe 5 are fixed at different positions of the fixation part 6, and the reproducibility of the measurement position is achieved by fixing the measurement probe 5 and the locating probe 4 at different positions. In the fourth case, the locating probe 4 and the measurement probe 5 are separated from the fixation part 6, the locating probe 4 and the measurement probe 5 are located at the same position, and the reproducibility of the measurement position is achieved by separating the measurement probe 5 from the fixation part 6.

According to the embodiments of the present disclosure, as shown in FIG. 12, FIG. 13 and FIG. 17 to FIG. 19, the above-mentioned system of measuring tissue element may further include the connector 7. The fixation part 6 is connected to the measurement probe 5 through the connector 7 so that the fixation part 6 is separated from the measurement probe 5; and/or the fixation part 6 is connected to the locating probe 4 through the connector 7 so that the fixation part 6 is separated from the locating probe 4.

According to the embodiments of the present disclosure, the connector 7 may be a hinge.

According to the embodiments of the present disclosure, the skin status of skin at the locating position and the measurement position may meet a first predetermined condition during a process of fixing the locating probe 4 and the measurement probe 5 to the fixation part 6.

According to the embodiments of the present disclosure, since the locating probe 4 and the measurement probe 5 may be fixed to the fixation part 6. The fixing of the locating probe 4 and the measurement probe to the fixation part 6 may affect the skin status of the skin at the corresponding position and thereby affecting the reproducibility of the measurement position. Therefore, in order to achieve the reproducibility of the measurement position, it is possible to make the skin status of the skin at the locating position and the measurement position meet the first predetermined condition during the process of fixing the locating probe 4 and the measurement probe 5 to the fixation part 6. That is, during the process of fixing the locating probe 4 and the measurement probe 5, the fixation part 6 ensures that the skin status of the skin at the locating position and the measurement position meets the first predetermined condition.

The first predetermined condition may mean that during the process of fixing the locating probe 4 and/or the measurement probe 5 to the fixation part 6, a change in the skin status of the skin at the corresponding position is within a predetermined range. Exemplarily, the change in the skin status may refer to a skin deformation. Accordingly, the first predetermined condition may refer to that the skin deformation at the corresponding position is within a predetermined deformation range during the process of fixing the locating probe 4 and/or the measurement probe 5 to the fixation part 6.

According to the embodiments of the present disclosure, as shown in FIG. 20 to FIG. 23, the fixation part 6 includes a fixation belt 60 and at least one fixation seat 61.

The fixation belt 60 is configured to fix each fixation seat 61. The fixation seat 61 is configured to fix the locating probe 4, so that the locating probe 4 is fixed by the fixation part 6. The fixation seat 61 is configured to fix the measurement probe 5, so that the measurement probe 5 is fixed by the fixation part 6.

According to the embodiments of the present disclosure, the fixation part 6 may include the fixation belt 60 and at least one fixation seat 61. The fixation belt 60 may fix each fixation seat 61, and the fixation belt 60 may be fixed at a position corresponding to the locating position and/or the measurement position. The locating probe 4 and the measurement probe 5 may be integrated or separated.

If the locating probe 4 is fixed to the fixation part 6, the locating probe 4 may be fixed to the fixation seat 61 in the fixation part 6. If the measurement probe 5 is fixed to the fixation part 6, the measurement probe 5 may be fixed to the fixation seat 61 in the fixation part 6. A number of fixation seats 61 may be set according to actual situations and is not limited here. Different fixation seats 61 may be connected through the connector 7, as shown in FIG. 20 to FIG. 23.

Figure 20:
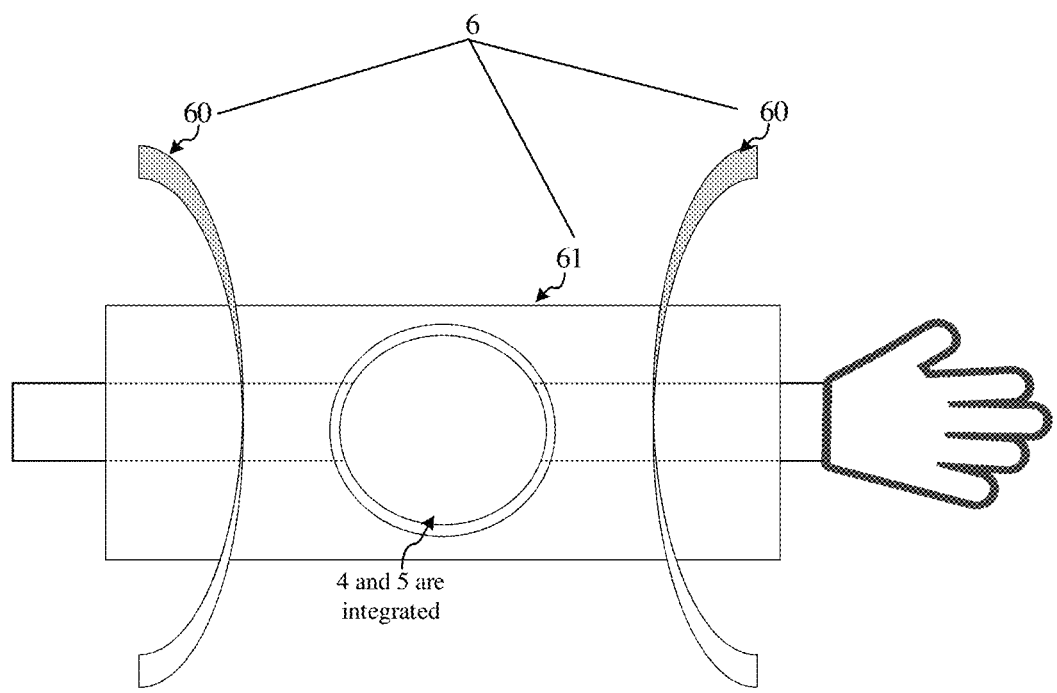
FIG. 20 is a schematic structural diagram of a fixation part in the embodiments of the present disclosure.
Figure 21:
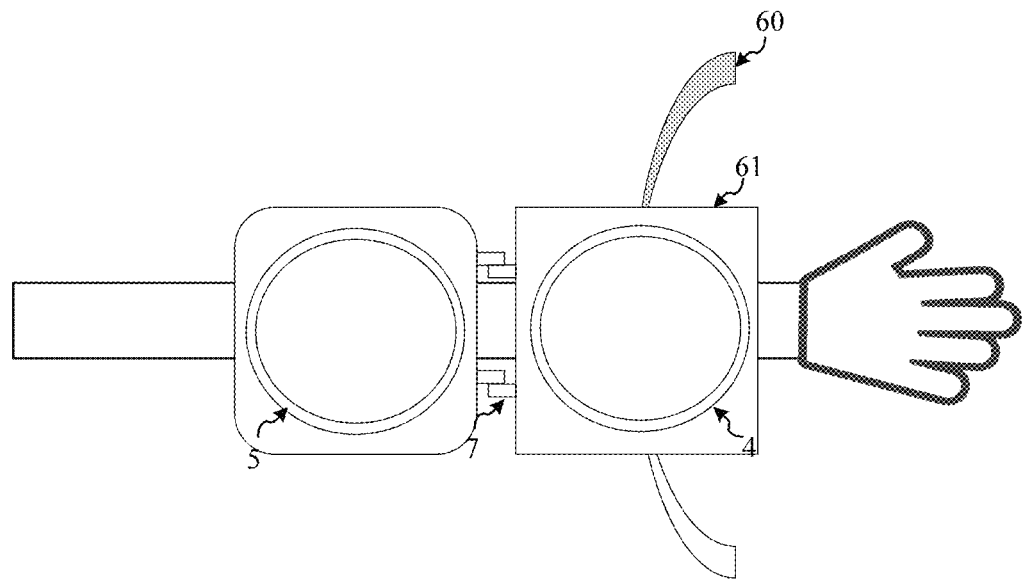
FIG. 21 is a schematic structural diagram of another fixation part in the embodiments of the present disclosure.
Figure 22:
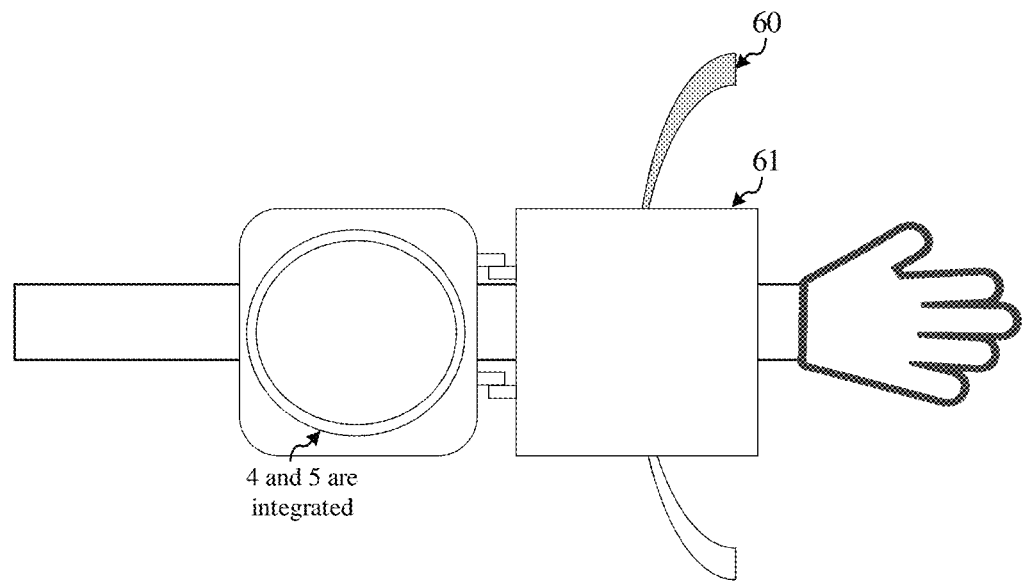
FIG. 22 is a schematic structural diagram of another fixation part in the embodiments of the present disclosure.
Figure 23:
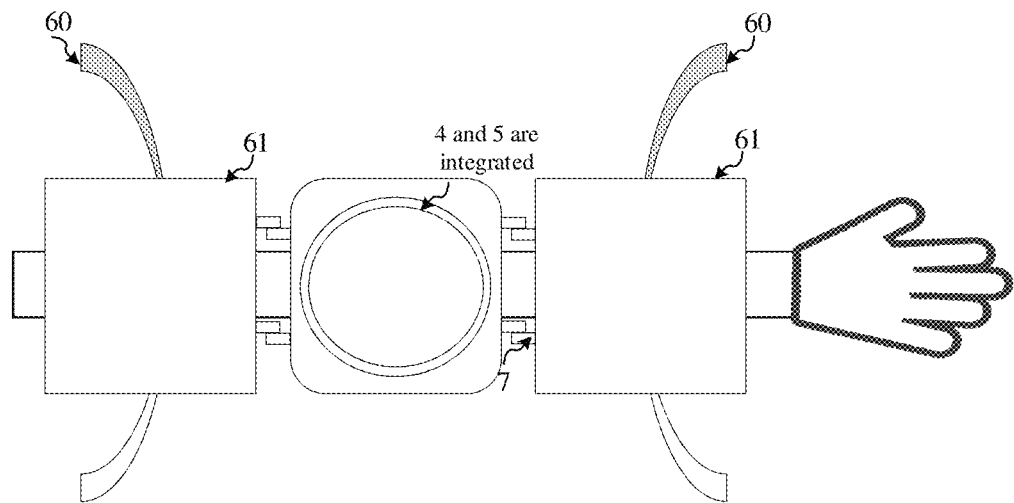
FIG. 23 is a schematic structural diagram of another fixation part in the embodiments of the present disclosure.

As shown in FIG. 20, a schematic structural diagram of a fixation part is given. In FIG. 16, the locating probe 4 and the measurement probe 5 may be integrated, and the integrated locating probe 4 and the measurement probe 5 are fixed to the fixation seat 61. As shown in FIG. 21, a schematic structural diagram of another fixation part is given. In FIG. 21, the locating probe 4 is separated from the measurement probe 5, the locating probe 4 is fixed to the fixation seat 61, and the measurement probe 5 is connected to the fixation seat 61 through the connector 7. As shown in FIG. 22, a schematic structural diagram of another fixation part is given. In FIG. 22, the locating probe 4 and the measurement probe 5 may be integrated, and the integrated locating probe 4 and the measurement probe 5 are separated from the fixation part 6, that is, the integrated locating probe 4 and the measurement probe 5 are not fixed to the fixation seat 61. The integrated locating probe 4 and the measurement probe 5 are connected to the fixation seat 61 through the connector 7. As shown in FIG. 23, a schematic structural diagram of another fixation part is given. FIG. 21 is different from FIG. 22 in that the fixation part 6 in FIG. 21 includes two fixation seats 61, so that the spectral data at the measurement position different from the locating position may be acquired.

According to the embodiments of the present disclosure, the skin status of the skin at the locating position and the measurement position may meet a second predetermined condition during a process of fixing each fixation seat 61 by the fixation belt 60.

According to the embodiments of the present disclosure, since an action of fixing the fixation seat 61 may affect the skin status of the skin at the corresponding position, and thereby affecting the reproducibility of the measurement position, it is possible to make the skin status of the skin at the locating position and the measurement position meet the second predetermined condition during the process of fixing each fixation seat 61 by the fixation belt 60 in order to ensure the reproducibility of the measurement position. That is, it is ensured that the skin status of the skin at the locating position and the measurement position meets the second predetermined condition during the process of fixing each fixation seat 61 by the fixation belt 60.

The second predetermined condition may refer to that, the change in the skin status at the corresponding position is within a predetermined range during the process of fixing each fixation seat 61 by the fixation belt 60. Exemplarily, the change in the skin status may refer to a skin deformation. Accordingly, the second predetermined condition may refer to that, the skin deformation at the corresponding position is within a predetermined deformation range during the process of fixing each fixation seat 61 by the fixation belt 60.

Figure 24:
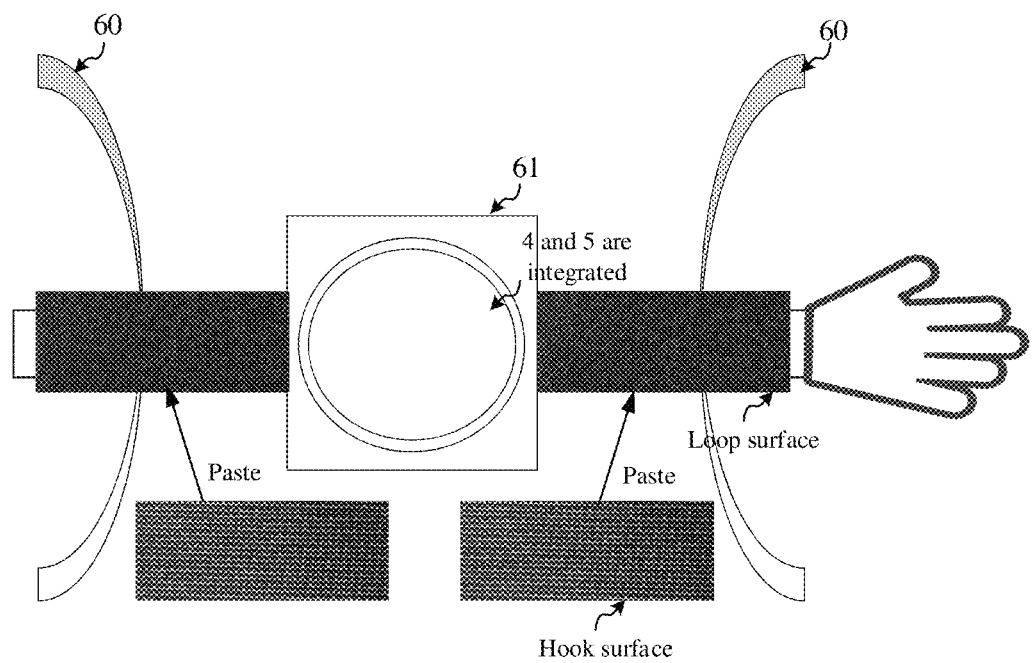
FIG. 24 is a schematic diagram of a fixation belt in the embodiments of the present disclosure.

According to the embodiments of the present disclosure, as shown in FIG. 24, a softness of the fixation belt 60 includes a first softness and a second softness, and the first softness is less than the second softness. The first softness is a corresponding softness during a process of fixing each fixation seat 61 by the fixation belt 60. The second softness is a corresponding softness after each fixation seat 61 is fixed by the fixation belt 60.

According to the embodiments of the present disclosure, in order to enable the fixation belt 60 to fix the locating probe 4 and/or the measurement probe 5, the fixation belt 60 is required to be rigid. At the same time, in order to reduce an influence of fixing of the locating probe 4 and/or the measurement probe 5 by the fixation belt 60 as much as possible, the fixation belt 60 is required to have a certain flexibility. As stated above, a requirement is put forward on the softness of the fixation belt 60.

In order to solve the above problems, it is possible to use change the softness of the fixation belt 60, that is, the softness of the fixation belt 60 includes the first softness and the second softness. The first softness represents the corresponding softness during the process of fixing each fixation seat 61 by the fixation belt 60, and the second softness represents the corresponding softness after each fixation seat 61 is fixed by the fixation belt 60, and the first softness is less than the second softness. As stated above, it may not only ensure that the fixation belt 60 achieves the fixing function, but also reduce the influence of fixing of the locating probe 4 and/or the measurement probe 5 by the fixation belt 60 as much as possible. For example, the fixation belt 60 is a Velcro or an elastic belt.

Exemplarily, as shown in FIG. 24, a schematic diagram of a fixation belt is given. The fixation belt 60 in FIG. 24 is the Velcro. Since a material of a loop surface of the Velcro is very soft, the influence of fixing of the locating probe 4 and/or the measurement probe 5 by the fixation belt 60 may be reduced. At this time, the softness of the fixation belt 60 is the first softness. Meanwhile, in order to enable the fixation belt to achieve the fixing function, after the locating probe 4 and/or the measurement probe 5 are/is fixed by the fixation belt 60, a hook surface may be pasted on the loop surface to increase the softness of the fixation belt 60. At this time, the softness of the fixation belt 60 is the second softness.

According to the embodiments of the present disclosure, since the corresponding softness during the process of fixing each fixation seat 61 by the fixation belt 60 is the first softness, the influence of fixing of the locating probe 4 and/or the measurement probe 5 by the fixation belt 60 may be reduced. Therefore, it may be ensured that the skin status of the skin at the locating position and the measurement position meets the second predetermined condition during the process of fixing each fixation seat 61 by the fixation belt 60.

According to the embodiments of the present disclosure, the fixation belt 60 is the Velcro or the elastic belt.

According to the embodiments of the present disclosure, a surface of the fixation belt 60 is provided with a hole.

According to the embodiments of the present disclosure, the softness of the fixation belt 60 is greater than or equal to a first softness threshold and less than or equal to a second softness threshold.

According to the embodiments of the present disclosure, in addition to the method described above, it is also possible to manufacture the fixation belt 60 using a material having a softness greater than or equal to the first softness threshold and less than or equal to the second softness threshold, which may also enable the fixation belt 60 to fix the locating probe 4 and/or the measurement probe 5 while reducing the influence of fixing of the locating probe 4 and/or the measurement probe 5 by the fixation belt 60 as much as possible. The first softness threshold and the second softness threshold may be set according to actual situations, and are not limited here.

Figure 25:
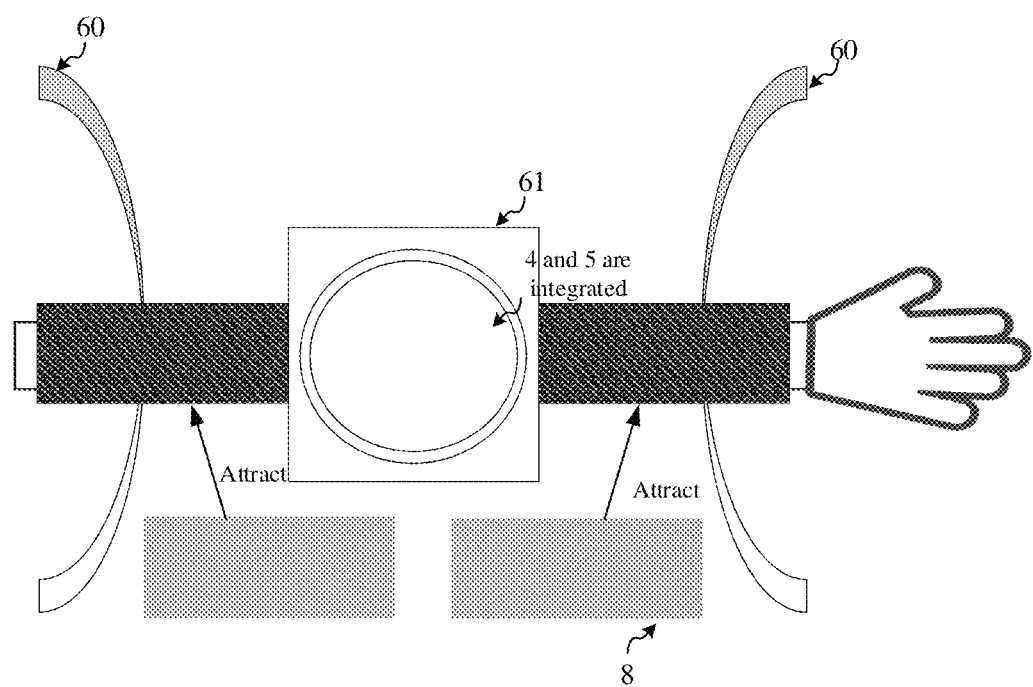
FIG. 25 is a schematic diagram of another fixation belt in the embodiments of the present disclosure.

According to the embodiments of the present disclosure, as shown in FIG. 25, the above-mentioned system of measuring tissue element may further include a magnetic part 8. An entire or partial fixation belt 60 is a metal hinge, and the magnetic part 8 cooperates with the fixation belt 60 to fix each fixation seat 61.

According to the embodiments of the present disclosure, in addition to the method described above, it is also possible to use a fixation belt 60 which is entirely or partially the metal hinge. Similarly, the fixation belt 60 may also fix the locating probe 4 and/or the measurement probe 5 while reducing the influence of fixing of the locating probe 4 and/or the measurement probe 5 by the fixation belt 60 as much as possible.

The fixing function is achieved as follows. After the fixation belt 60 completes fixing the locating probe 4 and/or the measurement probe 5, the magnetic part 8 may be attracted to the fixation belt 60, so that the magnetic part 8 cooperates with the fixation belt 60 to fix each fixation seat. As stated above, the fixing function may be achieved, and reference may be made to FIG. 25.

As shown in FIG. 25, a schematic diagram of another fixation belt is given. The fixation belt 60 in FIG. 25 is entirely the metal hinge. The magnetic part 8 may be attracted to the fixation belt 60 after the fixation belt 60 completes fixing the locating probe 4 and/or the measurement probe 5. The magnetic part 8 may be a miniature electromagnetic part 8. In addition, since the metal hinge is a ferromagnetic metal and a metal is easy to absorb heat, a direct contact between the metal hinge and the skin may produce a great influence on a skin temperature. Therefore, in order to avoid an influence of heat absorption of the metal on the skin temperature, it is possible to place a thermal insulator under the metal hinge. Optionally, the thermal insulator may be flannelette.

The above-mentioned content may be achieved because a good flexibility of the metal hinge may reduce the influence of the fixation belt 60 fixing the locating probe 4 and/or the measurement probe 5. Moreover, after the fixation belt 60 finishes fixing the locating probe 4 and/or the measurement probe 5, since the magnetic part 8 is attracted on the fixation belt 60, a cooperation of the two makes the fixation belt 60 become harder, and the fixing function may be achieved.

According to the embodiments of the present disclosure, the fixation belt 60 is entirely or partially the metal hinge, and a good flexibility of the metal hinge may reduce the influence of fixing of the locating probe 4 and/or the measurement probe 5 by the fixation belt 60. Therefore, it may be ensured that the skin status of the skin at the locating position and the measurement position meets the second predetermined condition during the process of fixing each fixation seat 61 by the fixation belt 60.

According to the embodiments of the present disclosure, the measurement probe does not move in the fixation seat during the process of collecting the current spectral data of the measurement position.

According to the embodiments of the present disclosure, when the measurement probe 5 is fixed to the fixation seat 6, there may also be a problem that the reproducibility of the measurement position is affected due to a weak fixing. In order to solve that problem, it may be ensured that the measurement probe 5 does not move in the fixation seat 61 during each current spectral measurement. That is, in each current spectral measurement, the current spectral data of the measurement position collected by the measurement probe 5 fixed to the fixed seat 61 is acquired, and the measurement probe 5 does not move in the fixation seat 61.

In addition, in each historical spectral measurement, the historical spectral data of the measurement position collected by the measurement probe 5 fixed to the fixation seat 61 is acquired, and the measurement probe 5 does not move in the fixation seat 61.

According to the embodiments of the present disclosure, the measurement probe 5 is fixed to the fixation seat 61 in at least one manner selected from: the measurement probe 5 being fixed to the fixation seat 61 by a double-sided adhesive tape, the measurement probe 5 being fixed to the fixation seat 61 by a fastener, the measurement probe 5 being fixed to the fixation seat 61 by a magnetic force, or a friction coefficient between the measurement probe 5 and the fixation seat 61 being greater than or equal to a friction coefficient threshold.

According to the embodiments of the present disclosure, in order to fix the measurement probe 5 to the fixation seat 61 and ensure that the measurement probe 5 does not move in the fixation seat 61, it is possible to use at least one of the following methods.

In a first method, the measurement probe 5 may be fixed to the fixation seat 61 by the double-sided adhesive tape. In a second method, the measurement probe 5 may be fixed to the fixation seat 61 by the fastener. In a third method, the measurement probe may be fixed to the fixation seat 61 by the magnetic force. In a fourth method, the friction coefficient between the measurement probe 5 and the fixation seat 61 is greater than or equal to the friction coefficient threshold. For example, a material of the fixation seat 61 may be rubber.

The embodiments of the present disclosure further provide a computer-readable storage medium having computer programs stored thereon. The programs, when executed by a processor, implement the method of measuring tissue element provided in the embodiments of the present disclosure. The method includes the following steps.

The target image information of the target position of the tissue to be measured and the pre-stored template image information of the locating position are acquired. The target image information includes the surface target image and/or the internal target image, and the template image information includes the surface template image and/or the internal template image. If the target image information is matched with the template image information, it is determined that the target position is the locating position. The measurement position is determined according to the locating position and the corresponding relationship between the locating position and the measurement position of the tissue to be measured.

The measurement position is the position meeting the reproducibility. The tissue element measurement is performed at the measurement position.

The computer storage medium in the embodiments of the present disclosure may be any combination of one or more computer-readable media. The computer-readable medium may be a computer-readable signal medium or a computer-readable storage medium. Herein, the computer-readable storage medium may be any tangible medium that contains or stores programs that may be used by or in combination with an instruction execution system, apparatus or device.

The computer-readable signal medium may contain data signals propagated in a baseband or as a part of a carrier wave, and computer-readable program codes are carried therein. Such propagated data signals may take various forms, including but not limited to electromagnetic signals, optical signals, or any suitable combination of the above. The computer-readable signal medium may also be any computer-readable medium other than the computer-readable storage medium. The computer-readable medium may send, propagate, or transmit programs for use by or in combination with the instruction execution system, apparatus or device.

The program codes contained on the computer-readable medium may be transmitted by any suitable medium, including but not limited to wireless, wired, optical cable, radio frequency, etc., or any suitable combination of the above.

Computer program codes used for performing operations of the present disclosure may be written in one or more programming languages, such as C language and Python, etc., or a combination thereof. The program codes may be executed on a computer or a server.

Certainly, for the computer-readable storage medium provided in the embodiments of the present disclosure, the computer-executable instructions thereof are not limited to the operations of the method described above, and related operations of the method of measuring tissue element for the electronic device provided in any embodiment of the present disclosure may also be performed. For introduction of the storage medium, reference may be made to the content explanation in the embodiments.

The specific embodiments of the present disclosure described above are not intended to limit the protection scope of the present disclosure. Any other corresponding changes and modifications made according to the technical concept of the present disclosure shall be included in the protection scope of the claims of the present disclosure.

What is claimed is:

1. A method of measuring tissue element, comprising:
    acquiring a target image information of a target position of a tissue to be measured and a pre-stored template image information of a locating position, wherein the target image information comprises a surface target image and an internal target image, the template image information comprises a surface template image and an internal template image, and the internal target image and the internal template image are images reflecting a dermis layer information;
    determining the target position as the locating position in response to the target image information being matched with the template image information;
    determining a measurement position according to the locating position and a corresponding relationship between the locating position and the measurement position of the tissue to be measured, wherein the measurement position is a position meeting a reproducibility, the corresponding relationship between the locating position and the measurement position comprises the measurement position being another position having a fixed positional relationship with the locating position, and the fixed positional relationship comprises a distance between the measurement position and the locating positing being within a predetermined distance range; and
    performing a tissue element measurement at the measurement position,
    wherein the target image information of the target position is acquired by using a locating probe, current spectral data of the measurement position is collected by using a measurement probe, the locating probe and the measurement probe are fixed to a fixation part, and in a process of fixing the locating probe and the measurement probe to the fixation part, a change in a skin status of skin at the locating position and the measurement position is within a predetermined range.

2. The method according to claim 1, wherein the performing a tissue element measurement at the measurement position comprises:
    performing a plurality of sets of current repeatability tests at the measurement position to determine a current evaluation parameter range; and
    performing the tissue element measurement at the measurement position in response to the current evaluation parameter range belonging to an expected evaluation parameter range, wherein the expected evaluation parameter range is an evaluation parameter range corresponding to a predetermined state of the measurement position.

3. The method according to claim 2, wherein the performing a plurality of sets of current repeatability tests at the measurement position to determine a current evaluation parameter range comprises:
    performing the plurality of sets of current repeatability tests at the measurement position to acquire current spectral data of the measurement position corresponding to each current spectral measurement, wherein each set of current repeatability tests comprises at least two current spectral measurements;
    determining, according to each current spectral data corresponding to each set of current repeatability tests, a current evaluation parameter corresponding to each set of current repeatability tests, wherein the current evaluation parameter is configured to evaluate a state of the measurement position; and
    determining the current evaluation parameter range according to each current evaluation parameter.

4. The method according to claim 3, wherein the acquiring a target image information of a target position of a tissue to be measured comprises:
    acquiring the target image information of the target position of the tissue to be measured collected by a locating probe.

5. The method according to claim 4, wherein the acquiring current spectral data of the measurement position corresponding to each current spectral measurement comprises:
    acquiring, in each current spectral measurement, the current spectral data of the measurement position collected by a measurement probe.

6. The method according to claim 4, further comprising:
    adjusting a position of the locating probe in response to the target image information being not matched with the template image information so as to acquire the target image information of another target position collected by the locating probe, until the target image information is matched with the template image information.

7. The method according to claim 1, wherein the determining the target position as the locating position in response to the target image information being matched with the template image information comprises:
   determining a similarity between the target image information and the template image information; and
   determining that the target image information is matched with the template image information and determining the target position as the locating position, in response to the similarity being greater than or equal to a similarity threshold.

8. The method according to claim 7, wherein the determining a similarity between the target image information and the template image information comprises:
   performing a correlation analysis on the target image information and the template image information to obtain a correlation coefficient; and
   determining the similarity between the target image information and the template image information according to the correlation coefficient.

9. An electronic device, comprising:
   one or more processors;
   a memory configured to store one or more programs;
   wherein the one or more programs, when executed by the one or more processors, cause the one or more processors to implement the method according to claim 1.

10. A system of measuring tissue element, comprising a locating probe, a measurement probe, and the electronic device according to claim 9;
    wherein the locating probe is configured to collect the target image information of the target position; and
    wherein the measurement probe is configured to collect current spectral data of the measurement position in each current spectral measurement.

11. The system according to claim 10, further comprising a fixation part; wherein a relationship between the fixation part and the locating probe and a relationship between the fixation part and the measurement probe are selected from:
    the fixation part being configured to fix the locating probe while being separated from the measurement probe;
    the fixation part being configured to fix the measurement probe while being separated from the locating probe;
    the fixation part being configured to fix the locating probe and the measurement probe while the locating probe and the measurement probe being fixed at a same position or different positions on the fixation part; or
    the fixation part being separated from the locating probe and the measurement probe.

12. The system according to claim 10, wherein a skin status of a skin at the locating position and the measurement position meets a first predetermined condition in a process of fixing the locating probe and the measurement probe to the fixation part.

13. The system according to claim 11, wherein the fixation part comprises a fixation belt and at least one fixation seat;
    wherein the fixation belt is configured to fix each fixation seat;
    wherein the fixation seat is configured to fix the locating probe, so that the locating probe is fixed by the fixation part; and
    wherein the fixation seat is further configured to fix the measurement probe, so that the measurement probe is fixed by the fixation part.

14. The system according to claim 13, wherein a skin status of a skin at the locating position and the measurement position meets a second predetermined condition in a process of fixing each fixation seat by the fixation belt.

15. The system according to claim 14, wherein a softness of the fixation belt comprises a first softness and a second softness; wherein the first softness is less than the second softness; wherein the first softness is a corresponding softness in the process of fixing each fixation seat by the fixation belt; and wherein the second softness is a corresponding softness after each fixation seat is fixed by the fixation belt.

16. The system according to claim 14, wherein a softness of the fixation belt is greater than or equal to a first softness threshold and less than or equal to a second softness threshold.

17. The system according to claim 14, further comprising a magnetic part; wherein the fixation belt is entirely or partially a metal hinge, and the magnetic part cooperates with the fixation belt to fix each fixation seat.

* * * * *